(12) United States Patent
Singh et al.

(10) Patent No.: US 7,994,276 B2
(45) Date of Patent: Aug. 9, 2011

(54) COMPOSITION OF TUMOUR-ASSOCIATED PEPTIDES AND RELATED ANTI-CANCER VACCINE

(75) Inventors: Harpreet Singh, Tubingen (DE); Steffen Walter, Dusslingen (DE); Toni Weinschenk, Aichwald (DE); Norbert Hilf, Kirchentellinsfurt (DE); Oliver Schoor, Tubingen (DE); Claudia Trautwein, Wuelfrath (DE); Peter Lewandrowski, Tuebingen-Hirschau (DE)

(73) Assignee: Immatics Biotechnologies GmbH, Tubingen (DE)

( * ) Notice: Subject to any disclaimer, the term of this patent is extended or adjusted under 35 U.S.C. 154(b) by 44 days.

(21) Appl. No.: 12/180,113

(22) Filed: Jul. 25, 2008

(65) Prior Publication Data

US 2009/0148400 A1    Jun. 11, 2009

Related U.S. Application Data

(60) Provisional application No. 60/953,109, filed on Jul. 31, 2007, provisional application No. 60/981,241, filed on Oct. 19, 2007.

(30) Foreign Application Priority Data

Jul. 27, 2007 (EP) .................... 07014796

(51) Int. Cl.
*A61K 38/00* (2006.01)
*A61K 38/04* (2006.01)
*C07K 4/00* (2006.01)
*C07K 7/00* (2006.01)
*C07K 14/00* (2006.01)
*A61P 35/00* (2006.01)

(52) U.S. Cl. ........ 530/300; 530/323; 530/326; 530/327; 530/328; 514/1.1; 514/19.2; 514/19.3; 514/19.4; 514/19.5

(58) Field of Classification Search .................. None
See application file for complete search history.

(56) References Cited

U.S. PATENT DOCUMENTS

| | | | |
|---|---|---|---|
| 6,096,313 | A | 8/2000 | Jager et al. |
| 6,623,923 | B1 | 9/2003 | Xu et al. |
| 6,756,038 | B1 * | 6/2004 | Schlom et al. ........ 424/185.1 |
| 2002/0102544 | A1 | 8/2002 | Mack et al. |
| 2003/0017167 | A1 | 1/2003 | Jiang |
| 2003/0105000 | A1 * | 6/2003 | Pero et al. ................ 514/12 |
| 2003/0109690 | A1 | 6/2003 | Ruben et al. |
| 2004/0171543 | A1 | 9/2004 | Dublanchet et al. |
| 2004/0265230 | A1 * | 12/2004 | Martinez et al. ........ 424/1.49 |

FOREIGN PATENT DOCUMENTS

| | | |
|---|---|---|
| EP | 1760089 | 3/2007 |
| WO | 0006723 | 2/2000 |
| WO | 03025138 | 3/2003 |
| WO | 2006027693 | 3/2006 |
| WO | WO 2009/015841 A1 * | 5/2009 |

OTHER PUBLICATIONS

Mologen Ag (dSLIM® Immunomdulators, 2010).*
Silver (The Immune Response Co. 2004).*
Linganu et al. (Expert Rev. Vaccines 2007: 6: 741-746).*
Pearse and Drane (Vaccine 2004 22:2391-2395).*
PRNewswire (Encoycopedia.com Mar. 1, 2006).*
Podda et al. (Expert Rev. Vaccines, 2003 2: 197-203).*
SEPPIC (www.montanide.com, 2010).*
ONTAK® (denileukin diftitox, package insert, Sep. 2009).*
Misseri, Y. (BT Pharma, S. A. 2007).*
Taunoton-Rigby (PRNewswire, Aquila Biopharmaceuticals, Inc. www.highbeam.com 1997).*
Celis (J. of Clinical Investigation, 2002, 110:1765-1768).*
Marincola et al. (Trends in Immunology, Jun. 2003, 334-341).*
Kirkin et al. (1998, APMIS, 106: 665-679).*
Sherman et al. (Critical Reviews in Immunol. 1998, 18:47-54).*
Smith (Clin. Immunol, 1994, 41(4): 841-849).*
Harlin et al. (Caner Immunol. Immunotherap. 2006, 55:1185-1197).*
Disis et al. (J. Immunol. 1996: 156:13151-3158).*
Gura (Science, 1997, 278:1041-1042).*
Kaiser (Science 2006, 31: 1370).*
Schellens et al. (Eur. J. Pharmaceutical Sciences 2000, 12:103-110).*
Taber's Cyclopedic Medical Dictionary (1985, F.A. Davis Company, Philadelphia, p. 274).*
Busken, C et al. (Digestive Disease Week Abstracts and Itinerary Planner, 2003, abstract No. 850).*
Krontiris and Capizzi (Internal Medicine, 4th Edition, Editor-in-chief Jay Stein, Elsevier Science, 1994 Chapters 71-72, pp. 699-729.*
Carter, S. K. et al. (Chemotherapy of Cancer; Second edition; John Wiley & Sons: New York, 1981; appendix C).*
Bowie et al (Science, 1990, 247:1306-1310).*
Skolnick et al. (TIBTECH 18:34-39, 2000).*
Ibragimova and Eade (Biophysical Journal, Oct. 1999, vol. 77, pp. 2191-2198).*
Rudikoff et al. (PNAS, USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Burgess et al (J. of Cell Bio. 111:2129-2138, 1990).*

(Continued)

*Primary Examiner* — Peter J Reddig
(74) *Attorney, Agent, or Firm* — Baker Donelson Bearman, Caldwell & Berkowitz PC

(57) ABSTRACT

The present invention relates to immunotherapeutic peptides and their use in immunotherapy, in particular the immunotherapy of cancer. The present invention discloses tumor-associated T-helper cell peptide epitopes, alone or in combination with other tumor-associated peptides that serve as active pharmaceutical ingredients of vaccine compositions which stimulate anti-tumor immune responses. In particular, the composition of the peptides of the present invention can be used in vaccine compositions for eliciting anti-tumor immune responses against colorectal cancer.

22 Claims, 7 Drawing Sheets

OTHER PUBLICATIONS

George et al. (2005, Trends in Immunology 26(12):653-659).*

International Search Report for PCT/EP2008/006152, Dated Jan. 7, 2009.

International Search Report for EP 05019255, Dated Dec. 1, 2005.

H. W. Heid et al.: "Apidpocyte Differentiation-Related Protein is Secreted Into Milk as a Constituent of Milk Lipid Globule Membrane", Biochemical Journal, Portland Press, London, GE, vol. 320, No. Part 3, Dec. 15, 1996, pp. 1025-1030, XP002060680, ISSN: 0264-6021; p. 1027; Figure 2.

J. Barnett et al.: "Production, Purification and Characterization of Human Matrilysin (Pump) From Recombinant Chinese Hamster Ovary Cells". Protein Expression and Purification, vol. 5, 1994, pp. 27-36, XP002352893, p. 34; Table 2.

A.R. Welch et al.: "Purification of Human Matrilysin Produced in *Escherichia coli* and Characterization Using a New Optimized Fluorogenic Peptide Substrate", Archives of Biochemistry and Biophysics, vol. 324, No. 1, 1995 pp. 59-64, XP002352894; p. 60; col. 1, Line 13-Line 17.

P. Brossart et al: "Identification of HLA-A2-Restricted T-Cell Epitopes Derived From the MUC1 Tumor Antigen for Broadly Applicable Vaccine Therapies", Blood, W.B. Saunders Company, Orlando, FL, US, vol. 93, No. 12, Jun. 15, 1999, pp. 4309-4317, XP 002147432, ISSN: 0006-4971, p. 4310, col. 1, Lin 53-Line 61.

* cited by examiner

A

B

COMPOSITION OF TUMOUR-ASSOCIATED PEPTIDES AND RELATED ANTI-CANCER VACCINE

RELATED APPLICATIONS

This application claims priority to European application number EP 07014796.2, filed on Jul. 27, 2007 and U.S. Provisional application Nos. 60/953,109, filed on Jul. 31, 2007 and 60/981,241, filed on Oct. 19, 2007, which are all incorporated by reference in their entirety. For the purposes of the present invention, all references as cited herein are incorporated by reference in their entireties.

FIELD OF THE INVENTION

The present invention relates to immunotherapeutic peptides and their use in immunotherapy, in particular the immunotherapy of cancer. The present invention discloses tumour-associated T-helper cell peptide epitopes, alone or in combination with other tumour-associated peptides that serve as active pharmaceutical ingredients of vaccine compositions, which stimulate anti-tumour immune responses. In particular, the composition of the peptides of the present invention can be used in vaccine compositions for eliciting anti-tumour immune responses against colorectal cancer.

BACKGROUND OF THE INVENTION

Colorectal Carcinoma

According to the American Cancer Society, colorectal cancer (CRC) is the third most common cancer in the US, afflicting more than 175,000 new patients each year. In the US, Japan, France, Germany, Italy Spain and the UK, it affects more than 480,000 patients. It is one of the most common causes of cancer mortality in developed countries.

Research suggests that the onset of colorectal cancer is the result of interactions between inherited and environmental factors. In most cases, adenomatous polyps appear to be precursors to colorectal tumours; however the transition may take many years. The primary risk factor for colorectal cancer is age, with 90% of cases diagnosed over the age of 50 years. Other risk factors for colorectal cancer according to the American Cancer Society include alcohol consumption, a diet high in fat and/or red meat and an inadequate intake of fruits and vegetables. Incidence continues to rise, especially in areas such as Japan, where the adoption of westernized diets with excess fat and meat intake and a decrease in fiber intake may be to blame. However, incidence rates are not rising as fast as before, which may be due to increased screening and polyp removal, thus preventing progression of polyps to cancer.

As in most solid tumours, first line treatment is surgery, however, its benefits remain confined to early-stage patients, yet a significant proportion of patients is diagnosed in advanced stages of the disease. For advanced colorectal cancer, chemotherapy regimens based on fluorouracil-based regimens are the standard of care. The majority of these regimens are the so-called FOLFOX (infusional 5-FU/leucovorin plus oxaliplatin) and FOLFIRI (irinotecan, leucovorin, bolus and continuous-infusion 5-FU) protocols.

The introduction of third-generation cytotoxics such as irinotecan and oxaliplatin has raised the hope of significantly improving efficacy, but prognosis is still relatively poor, and the survival rate generally remains at approximately 20 months in metastatic.

Recently, a novel generation of drugs, molecular-targeted agents, such as Avastin® (bevacizumab) and Erbitux® (cetuximab), became available and about 40 compounds are in late-stage clinical development for different stages of colorectal cancer. Combinations of several of these compounds increase the number of potential treatment options expected for the future. The vast majority of substances is in phase 2, with EGFR addressed by these compounds more often than by any other drug in development for colorectal cancer, which is due to the fact that in ~80% of patients with colorectal cancer EGFR expression is upregulated.

Clinical trials with stage II patients combining chemotherapy with the recently approved monoclonal antibodies (mAbs) (cetuximab +irinotecan or FOLFOX4; bevacizumab as a single-agent or together with FOLFOX4) are currently being conducted. Three to four year observation periods are expected for statistically significant results from these trials.

Monoclonal antibodies (mAbs) presently used in oncology generally have an excellent chance of not interfering with active immunotherapy. In fact, there is preclinical evidence suggesting that depletion of VEGF (by bevacizumab) contributes positively to DC-mediated activation of T-cells.

Currently there are about 16 trials testing the safety and potential of novel immunotherapeutic approaches for the treatment of CRC.

Immunotherapeutic Approaches for Treatment

Stimulation of an immune response is dependent upon the presence of antigens recognized as foreign by the host immune system. The discovery of the existence of tumour associated antigens has now raised the possibility of using a host's immune system to intervene in tumour growth. Various mechanisms of harnessing both the humoral and cellular arms of the immune system are currently being explored for cancer immunotherapy.

Specific elements of the cellular immune response are capable of specifically recognizing and destroying tumour cells. The isolation of cytotoxic T-cells (CTL) from tumour-infiltrating cell populations or from peripheral blood suggests that such cells play an important role in natural immune defences against cancer (Cheever et al., Annals N.Y. Acad. Sci. 1993 690:101-112; Zeh H J, et al., J Immunol. 1999, 162(2):989-94). CD8-positive T-cells (TCD8$^+$) in particular, which recognize Class I molecules of the major histocompatibility complex (MHC)-bearing peptides of usually 8 to 10 residues derived from proteins or defect ribosomal products (DRIPS) (Schubert U, et al., Nature 2000; 404(6779):770-774) located in the cytosols, play an important role in this response. The MHC-molecules of the human are also designated as human leukocyte-antigens (HLA).

There are two classes of MHC-molecules. MHC class I molecules can be found on most cells having a nucleus and present peptides that result from proteolytic cleavage of endogenous proteins, defective ribosomal product (DRiPS), and larger peptides. MHC class II molecules can be found predominantly on professional antigen presenting cells (APCs), and present peptides of exogenous proteins that are taken up by APCs during the course of endocytosis, and are subsequently processed. Complexes of peptide and MHC class I molecule are recognized by CD8-positive cytotoxic T-lymphocytes bearing the appropriate T-cell receptors (TCR). Complexes of peptide and MHC class II molecule are recognized by CD4-positive-helper-T-cells bearing the appropriate TCR.

CD4-positive helper T-cells play an important role in orchestrating the effector functions of anti-tumour T-cell responses and, for this reason, the identification of CD4-positive T-cell epitopes derived from tumour associated antigens (TAA) may be of great importance for the development of pharmaceutical products for triggering anti-tumour immune responses (Kobayashi, H., et al., 2002. Clin. Cancer Res. 8:3219-3225; Gnjatic, S., et al., 2003. Proc. Natl. Acad. Sci. U.S.A. 100(15):8862-7). CD4+ T cells can lead to locally increased levels of IFNγ (Qin Z, et al., Cancer Res. 2003 J; 63(14):4095-4100).

It was shown in mammalian animal models, e.g., mice, that even in the absence of cytotoxic T lymphocyte (CTL) effector cells (i.e., CD8-positive T lymphocytes), CD4 positive T-cells are sufficient for inhibiting manifestation of tumours via inhibition of angiogenesis by secretion of interferon-gamma (IFNγ) (Qin, Z., et al., 2000. Immunity. 12:677-686). Additionally, it was shown that CD4 positive T-cells recognizing peptides from tumour-associated antigens presented by HLA class II molecules can counteract tumour progression via the induction of an antibody (Ab) responses (Kennedy, R. C., et al., 2003. Cancer Res. 63:1040-1045). In contrast to tumour-associated peptides binding to HLA class I molecules, only a small number of class II ligands of TAA have been described so far. See generally, the syfpeithi database listing known MHC ligands and peptide motifs and Cancer Immunity, the Journal of Academy of Cancer Immunology.

Since the constitutive expression of HLA class II molecules is usually limited to cells of the immune system (Mach, B., et al., 1996. Annu. Rev. Immunol. 14:301-331), the possibility of isolating class II peptides directly from primary tumours was not considered possible. However, the inventors were recently successful in identifying a number of MHC Class II epitopes directly from tumours (EP 04 023 546.7, EP 05 019 254.1; Dengjel J, et al., Clin Cancer Res. 2006; 12:4163-4170).

In the absence of inflammation, expression of MHC class II molecules is mainly restricted to cells of the immune system, especially professional antigen-presenting cells (APC), e.g., monocytes, monocyte-derived cells, macrophages, dendritic cells. In tumour patients, cells of the tumour have surprisingly been found to express MHC class II molecules (Dengjel J, et al., Clin Cancer Res. 2006; 12:4163-4170).

For a peptide to trigger (elicit) a cellular immune response, it must bind to an MHC-molecule. This process is dependent on the allele of the MHC-molecule and specific polymorphisms of the amino acid sequence of the peptide. MHC-class-I-binding peptides are usually 8-10 amino acid residues in length and usually contain two conserved residues ("anchor") in their sequence that interact with the corresponding binding groove of the MHC-molecule. In this way each MHC allele has a "binding motif" determining which peptides can bind specifically to the binding groove (Rammensee, H G, et al., 1997, MHC Ligands and Peptide Motifs).

In the MHC class I dependent immune reaction, peptides not only have to be able to bind to certain MHC class I molecules expressed by tumour cells, they also have to be recognized by T-cells bearing specific T-cell receptors (TCR).

The antigens that are recognized by the tumour specific T-lymphocytes, that is, their epitopes, can be molecules derived from all protein classes, such as enzymes, receptors, transcription factors, etc. Furthermore, tumour associated antigens, for example, can also be present in tumour cells only, for example as products of mutated genes. Another important class of tumour associated antigens are tissue-specific antigens, such as CT ("cancer testis")-antigens that are expressed in different kinds of tumours and in healthy tissue of the testis.

Various tumour associated antigens have been identified. Further, much research effort is being expended to identify additional tumour associated antigens. Some groups of tumour associated antigens, also referred to in the art as tumour specific antigens, are tissue specific. Examples include, but are not limited to, tyrosinase for melanoma, PSA and PSMA for prostate cancer and chromosomal cross-overs (translocations) such as bcr/abl in lymphoma. However, many tumour associated antigens identified occur in multiple tumour types, and some, such as oncogenic proteins and/or tumour suppressor genes (tumour suppressor genes are, for example reviewed for renal cancer in Linehan W M, et al., J Urol. 2003 Dec; 170(6 Pt 1):2163-72), which actually cause the transformation event, occur in nearly all tumour types. For example, normal cellular proteins that control cell growth and differentiation, such as p53 (which is an example for a tumour suppressor gene), ras, c-met, myc, pRB, VHL, and HER-2/neu, can accumulate mutations resulting in upregulation of expression of these gene products thereby making them oncogenic (McCartey et al. Cancer Research 1998 15:58 2601-5; Disis et al. Ciba Found. Symp. 1994 187:198-211). These mutant proteins can also be a target of a tumour specific immune response in multiple types of cancer.

Immunotherapy in cancer patients aims at activating cells of the immune system specifically, especially the so-called cytotoxic T-cells (CTL, also known as "killer cells," also known as CD8-positive T-cells), against tumour cells but not against healthy tissue. Tumour cells differ from healthy cells by the expression of tumour-associated proteins. HLA molecules on the cell surface present the cellular content to the outside, thus enabling a cytotoxic T cell to differentiate between a healthy and a tumour cell. This is realized by breaking down all proteins inside the cell into short peptides, which are then attached to HLA molecules and presented on the cell surface (Rammensee, H G, et al., 1993, Annu. Rev. Immunol., 11, 213-244). Peptides that are presented on tumour cells, but not presented, or to a far lesser extent, on healthy cells of the body, are called tumour-associated peptides (TUMAPs).

For proteins to be recognized by cytotoxic T-lymphocytes as tumour-specific or —associated antigens, and to be used in a therapy, particular prerequisites must be fulfilled. The antigen should be expressed mainly by tumour cells and not by normal healthy tissues or in comparably small amounts. It is furthermore desirable, that the respective antigen is not only present in a type of tumour, but also in high concentrations (i.e. copy numbers of the respective peptide per cell). Tumour-specific and tumour-associated antigens are often derived from proteins directly involved in transformation of a normal cell to a tumour cell due to a function e.g. in cell cycle control or apoptosis. Additionally, also downstream targets of the proteins directly causative for a transformation may be upregulated and thus be indirectly tumour-associated. Such indirectly tumour-associated antigens may also be targets of a vaccination approach. In both cases the presence of epitopes in the amino acid sequence of the antigen is essential, since such peptide ("immunogenic peptide") that is derived from a tumour associated antigen should lead to an in vitro or in vivo T-cell-response.

Basically, any peptide able to bind a MHC molecule may function as a T-cell epitope. A prerequisition for the induction of an in vitro or in vivo T-cell-response is the presence of a T-cell with a corresponding T-cell receptor ("TCR") and the absence of tolerance for this particular epitope.

T-helper cells play an important role in orchestrating the effector function of CTLs in anti-tumour immunity. T-helper cell epitopes that trigger a T-helper cell response of the TH1 type support effector functions of CD8-positive Killer T-cells, which include cytotoxic functions directed against tumour cells displaying tumour-associated peptide/MHC complexes on their cell surfaces. In this way tumour-associated T-helper cell peptide epitopes, alone or in combination with other tumour-associated peptides, can serve as active pharmaceutical ingredients of vaccine compositions which stimulate anti-tumour immune responses.

Since both types of response, CD8 and CD4 dependent, contribute jointly and synergistically to the anti-tumour effect, the identification and characterization of tumour-associated antigens recognized by either CD8+ CTLs (MHC class I molecule) or by CD4-positive CTLs (MHC class II molecule) is important in the development of tumour vaccines. It is therefore an object of the present invention, to provide compositions of peptides that contain peptides binding to MHC complexes of either class.

The first clinical trials using tumour-associated peptides started in the mid-1990s by Boon and colleagues mainly for the indication melanoma. Clinical responses in the best trials have ranged from 10% to 30%. Severe side effects or severe autoimmunity, however, have not been reported in any clinical trial using peptide-based vaccine monotherapy. Mild forms of vitiligo have been reported for some patients who had been treated with melanoma-associated peptides.

However, priming of one kind of CTL is usually insufficient to eliminate all tumour cells. Tumours are very mutagenic and thus able to rapidly respond to CTL attacks by changing their protein pattern to evade recognition by CTLs. To counter-attack the tumour evasion mechanisms a variety of specific peptides is used for vaccination. In this way a broad simultaneous attack can be mounted against the tumour by several CTL clones. This may decrease the opportunities for the tumour to evade the immune response. This hypothesis has been recently confirmed in a clinical study treating late-stage melanoma patients. With only few exceptions, patients that had at least three distinct T-cell responses, showed objective clinical responses or stable disease (Banchereau, J, et al., 2001, Cancer Res., 61, 6451-6458) as well as increased survival (personal communication with J. Banchereau), while the vast majority of patients with less than three T-cell responses were diagnosed with progressive disease.

A study by the inventors of the present invention showed a similar effect when patients suffering from renal cell carcinoma were treated with a vaccine composed of 13 different peptides (H. Singh-Jasuja, et al., ASCO Meeting 2007 Poster # 3017; M. Staehler, et al., ASCO meeting 2007; Poster # 3017).

The major task in the development of a tumour vaccine is therefore the not only the identification and characterization of novel tumour associated antigens and immunogenic T-helper epitopes derived thereof, but also the combination of different epitopes to increase the likelihood of a response to more than one epitope for each patient. It is therefore an object of the present invention to provide combinations of amino acid sequences of peptides that have the ability to bind to a molecule of the human major histocompatibility complex (MHC) class-I (HLA class I) or II (HLA class II). It is a further object of the present invention, to provide an effective anti-cancer vaccine that is based on a combination of the peptides.

In the present invention, the inventors isolated and characterized peptides binding to HLA class I or II molecules directly from mammalian tumours, i.e. colorectal carcinomas.

SUMMARY OF THE INVENTION

The present invention relates to immunotherapeutic peptides and their use in immunotherapy, in particular the immunotherapy of cancer. The present invention discloses tumour-associated T-helper cell peptide epitopes, alone or in combination with other tumour-associated peptides that serve as active pharmaceutical ingredients of vaccine compositions that stimulate anti-tumour immune responses. In particular, compositions of the peptides of the present invention can be used in vaccine compositions for eliciting anti-tumour immune responses against colorectal cancer.

The present invention provides pharmaceutical compositions comprising at least two peptides containing an amino acid sequence selected from the group consisting of SEQ ID NO: 1 to SEQ ID NO: 7, and/or containing a variant amino acid sequence that is at least 80% identical to that of SEQ ID NO: 1 to SEQ ID NO: 7, and/or a polynucleotide containing a nucleic acid encoding SEQ ID NO: 1 to SEQ ID NO: 7 or the variant amino acid sequence, and a pharmaceutically acceptable carrier. One embodiment of the present invention provides a CEA-004 peptide (SEQ ID NO: 15). In another embodiment, the sequence of the CEA-004 peptide is altered in position 6 to D, N or C and/or on position 7 to I.

Pharmaceutical compositions of the present invention may also further comprise at least one additional peptide containing an amino acid sequence selected from the group consisting of SEQ ID NO: 8 to SEQ ID NO: 15, or containing a variant amino acid sequence that is at least 80% identical to that of SEQ ID NO: 8 to SEQ ID NO: 15, or polynucleotide containing a nucleic acid encoding SEQ ID NO: 8 to SEQ ID NO: 15 or the variant amino acid sequence. The peptides may have an overall length of between 8 and 100, preferably between 8 and 30, and most preferably between 8 and 16 amino acids. The peptides may also have non-peptide bonds.

The present invention also provides pharmaceutical compositions described above wherein they comprise at least two peptides consisting of amino acid sequences according to SEQ ID NO: 1 to SEQ ID NO: 15.

In certain pharmaceutical compositions of the invention, the selection, number and/or amount of peptides present in the composition is/are tissue, cancer, and/or patient-specific.

Pharmaceutical compositions of the invention may further comprise at least one suitable adjuvant. The adjuvant may be, but is not limited to, 1018 ISS, aluminium salts, Amplivax, AS15, BCG, CP-870,893, CpG7909, CyaA, dSLIM, GM-CSF, IC30, IC31, Imiquimod, ImuFact IMP321, IS Patch, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel vector system, PLG microparticles, resiquimod, SRL172, Virosomes and other Virus-like particles, YF-17DBCG, Aquila's QS21 stimulon, Ribi's Detox. Quil, Superfos, Freund's, GM-CSF, cholera toxin, immunological adjuvants, MF59, and cytokines. In certain preferred embodiments, the adjuvant may be colony-stimulating factors, such as Granulocyte Macrophage Colony Stimulating Factor (GM-CSF).

In certain embodiments, pharmaceutical compositions of the invention additionally contain at least one antigen presenting cell, which may be a dendritic cell. The antigen presenting cell may be pulsed or loaded with a peptide of the present invention or may comprise an expression construct encoding a peptide of the present invention.

Pharmaceutical compositions of the invention may be administered as a vaccine, which can be administered any appropriate route, such as intravenously, intra-arterially, intra-peritoneally, intramuscularly, intradermally, intratumorally, orally, dermally, nasally, buccally, rectally, vaginally, by inhalation, or by topical administration.

The present invention also provides mehods for treating or preventing a cancer in a patient comprising administering to the patient a therapeutically effective amount of a pharmaceutical composition of the present invention. Pharmaceutical compositions may be used as an anti-cancer vaccine. The cancer may be a cancer of the buccal cavity and pharynx, cancer of the digestive tract, cancer of the colon, rectum, and anus, cancer of the respiratory tract, breast cancer, cancer of the cervix uteri, vagina, and vulva, cancer of the uterine corpus and ovary, cancer of the male genital tract, cancer of the urinary tract, cancer of the bone and soft tissue, and Kaposi sarcoma, melanoma of the skin, eye melanoma, and non-melanoma eye cancer, cancer of the brain and central nervous system, cancer of the thyroid and other endocrine glands, Hodgkin Lymphoma, Non-Hodgkin Lymphoma, and myeloma, preferably renal cancer, colorectal cancer, lung cancer, breast cancer, pancreatic cancer, prostate cancer, gastric cancer, GIST or glioblastoma. In certain embodiments, the cancer is colorectal cancer.

DETAILED DESCRIPTION OF THE INVENTION

Figure 1:
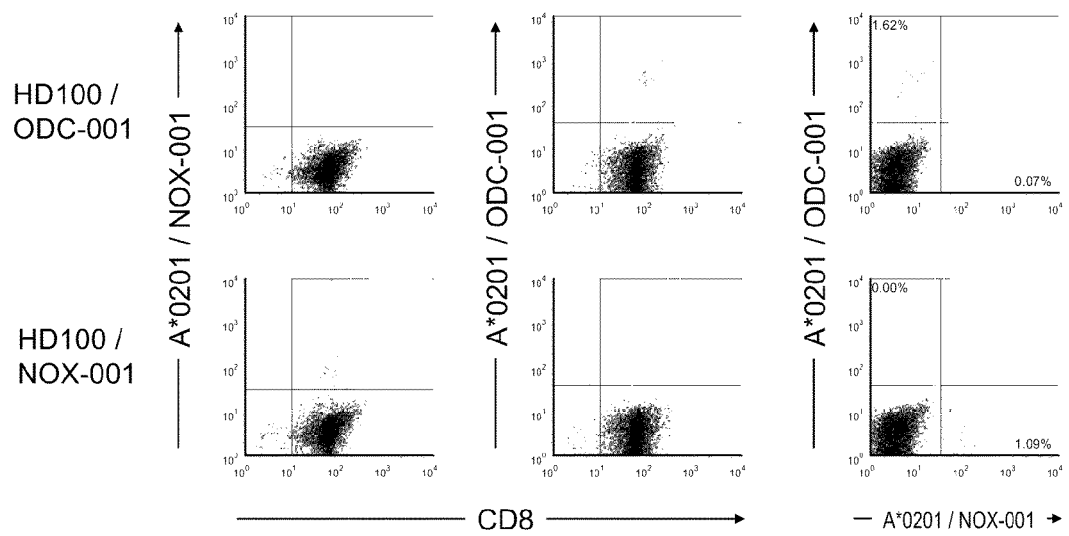
FIG. 1: Tetramer analysis of microsphere driven proliferation of ODC-001 and NOX-001 specific CD8+ lymphocytes from peripheral blood. $1 \times 10^6$ CD8+ enriched PBMCs per well of the healthy HLA-A*0201+ donor HD100 was stimulated weekly with microspheres coupled to anti-CD28 plus high densitiy tumor antigen A*0201/ODC-001 (upper panel) or anti-CD28 plus high densitiy tumor antigen A*0201/NOX-001 (lower panel). After three stimulations in vitro, all cells were stained with antibody CD8 FITC plus tetramers A*0201/NOX-001 PE and A*0201/ODC-001 APC. Cells are gated on the lymphocyte population or CD8+ lymphocytes (right panel) and numbers represent percentage of tetramer+ within CD8+ lymphocytes.

The present invention provides peptides that stem from antigens associated with tumourigenesis, and have the ability to bind sufficiently to MHC (HLA) class II molecules for triggering an immune response of human leukocytes, especially lymphocytes, especially T lymphocytes, especially CD4-positive T lymphocytes, especially CD4-positive T lymphocytes mediating $T_{HI}$-type immune responses.

The present invention also provides peptides that stem from antigens associated with tumourigenesis, and have the ability to bind sufficiently to MHC (HLA) class I molecules for triggering an immune response of human leukocytes, especially lymphocytes, especially T lymphocytes, especially CD8-positive cytotoxic T-lymphocytes as well as combinations of the two that are particularly useful for vaccination of patients that suffer from cancer.

According to the present invention, the object is solved by providing a pharmaceutical composition comprising at least two peptides containing an amino acid sequence selected from the group consisting of SEQ ID NO: 1 to SEQ ID NO: 7, and/or containing a variant amino acid sequence that is at least 80% homologous to that of SEQ ID NO: 1 to SEQ ID NO: 7, and/or a polynucleotide containing a nucleic acid encoding SEQ ID NO: 1 to SEQ ID NO: 7 or the variant amino acid sequence, and a pharmaceutically acceptable carrier.

As described herein below, the peptides that form the basis of the present invention have all been identified as presented by MHC class I or II bearing cells. Thus, these particular peptides, as well as other peptides containing the sequence (i.e. derived peptides), all elicit a specific T-cell response, although the extent to which such response will be induced might vary from individual peptide to peptide and from individual patient to patient. Differences, for example, could be caused due to mutations in the peptides. The person of skill in the present art is well aware of methods that can be applied to determine the extent to which a response is induced by an individual peptide, in particular with reference to the examples herein and the respective literature.

Preferably the variants of the invention will induce T-cells cross-reacting with the respective peptide of the invention. The percentage of homology between the amino acid sequence of a peptide or a nucleic acid sequence encoding the peptide and a variant can be calculated using algorithms well known in the art. In the present invention, the term "homologous" refers to the degree of identity between sequences of two amino acid sequences, i.e. peptide or polypeptide sequences. The aforementioned "homology" is determined by comparing two sequences aligned under optimal conditions over the sequences to be compared. The amino acid or nucleic acid sequences to be compared herein may have an addition or deletion (for example, gap and the like) in the optimum alignment of the two sequences. Such a sequence homology can be calculated by creating an alignment using, for example, ClustalW algorithm (Nucleic Acid Res., 22(22): 4673 4680 (1994). Commonly available sequence analysis software, more specifically, Vector NTI, GENETYX or analysis tools provided by public databases may also be used.

Pharmaceutically acceptable carriers are well known and are usually liquids, in which an active therapeutic agent is formulated. The carrier generally does not provide any pharmacological activity to the formulation, though it may provide chemical and/or biological stability, release characteristics, and the like. Exemplary formulations can be found, for example, in Alfonso R. Gennaro. Remington: The Science and Practice of Pharmacy, 20th Edition. Baltimore, Md.: Lippincott Williams & Wilkins, 2000 and include, but are not limited to, saline, water, buffered water, 0.3% glycine, hyaluronic acid, dextrose and the like. Recently, it was found that certain fat emulsions, which have been in use for many years for intravenous nutrition of human patients, can also act as a vehicle for peptides. Two examples of such emulsions are the available commercial fat emulsions known as Intralipid® and Lipofundin®. "Intralipid®" is a registered trademark of Kabi Pharmacia, Sweden, for a fat emulsion for intravenous nutrition, described in U.S. Pat. No. 3,169,094. "Lipofundint" is a registered trademark of B. Braun Melsungen, Germany. Both contain soybean oil as fat (100 or 200 g in 1,000 ml distilled water: 10% or 20%, respectively). Egg-yolk phospholipids are used as emulsifiers in Intralipid® (12 g/l distilled water) and egg-yolk lecithin in Lipofundin® (12 g/l distilled water). Isotonicity results from the addition of glycerol (25 g/l) both in Intralipid® and Lipofundin®.

The peptides stem from tumour-associated antigens, especially tumour-associated antigens with functions in, e.g., proteolysis, angiogenesis, cell growth, cell cycle regulation, cell division, regulation of transcription, regulation of translation, tissue invasion, etc. Table 1 provides the peptides and the function of the protein from which the peptides are derived.

In the context of cancer, C20orf42 has been described within studies investigating gene expression in cancer-relevant settings. It was found to be overexpressed in 70% of colon carcinomas and 60% of lung carcinomas tested (n=10). Normal tissue expression by Northern Blot was restricted to neuromuscular tissues (Weinstein, E J, et al., 2003, Biochim. Biophys. Acta, 1637, 207-216). Furthermore, C20orf42 has been identified as a gene involved in TGF-β-mediated cell migration and tumour invasion (Kloeker, S, et al., 2004, J. Biol. Chem., 279, 6824-6833).

NADPH Oxidase Homolog-1 (NOX1)

NOX1, is a growth factor-responsive enzyme that catalyzes formation of the reactive oxygen species superoxide ($O_2^-$) and hydrogen peroxide ($H_2O_2$). Its expression was originally identified in colon, prostate, uterus, and proliferating vascular smooth muscle cells (Suh, Y. A. et al. (1999) Nature 401, 79-82). Its expression is linked to a number of biological responses including cellular proliferation, angiogenesis, and activation of cellular signaling pathways (Harper, R. et al., 2005, Arch. Biochem. Biophys. 435, 323-330).

NOX1 is highly expressed in the colon but its function in colonic physiology or pathology is still poorly understood. In normal tissues, NOX1 expression was low in the ileum, intermediate in the right colon, and high in the left colon. There was no statistical difference in NOX1 expression between samples derived from adenomas, well differentiated or poorly differentiated colon adenocarcinomas. NOX1 was highly expressed in colon epithelial cells, both within the crypts and on the luminal surface. In conclusion, NOX1 is an enzyme

TABLE 1

Peptides of the present invention and function of the parent protein

| SEQ ID NO: | Peptide ID | Sequence | Gene Symbol | Function | binds to MHC |
|---|---|---|---|---|---|
| 1 | C20-001 | ALSNLEVTL | C20orf42 | implicated in linking actin cytoskeleton to ECM | HLA-A*02 |
| 2 | NOX-001 | ILAPVILYI | NOX1 | NADPH oxidase | HLA-A*02 |
| 3 | ODC-001 | ILDQKINEV | ODC1 | Ornithine decarboxylase | HLA-A*02 |
| 4 | PCN-001 | KLMDLDVEQL | PCNA | DNA polymerase delta auxiliary protein | HLA-A*02 |
| 5 | TGFBI-001 | ALFVRLLALA | TGFBI | transforming growth factor, beta-induced | HLA-A*02 |
| 6 | TOP-001 | KIFDEILVNA | TOP2A/TOP2B | Topoisomerase | HLA-A*02 |
| 7 | TGFBI-004 | TPPIDAHTRNLLRNH | TGFBI | transforming growth factor, beta-induced | HLA-DR |

Chromosome 20 Open Reading Frame 42

C20orf42 is a focal adhesion protein involved in attachment of the actin cytoskeleton to the plasma membrane and in integrin-mediated cellular processes. Deficiency of C20orf42 as a result of loss-of-function mutations causes Kindler syndrome, an autosomal recessive genodermatosis characterized by skin blistering, progressive skin atrophy, photosensitivity and, occasionally, carcinogenesis (Herz, C, et al., 2006, J Biol Chem., 281, 36082-36090). Recently, a severe gastrointestinal tract involvement with hemorrhagic colitis has been reported in a patient with a loss-of-function mutation (Sadler, E, et al., 2006, Arch. Dermatol., 142, 1619-1624).

that is constitutively expressed in colon epithelium and is not directly associated with tumourigenesis (Szanto, I. et al. 2005, J Pathol. 207, 164-176).

Immunohistochemistry showed that NOX1 was constitutively expressed in surface mucous cells. Adenomas and well differentiated adenocarcinomas up-regulated NOX1 expression. Nuclear factor (NF)-kappaB was predominantly activated in adenoma and adenocarcinoma cells expressing abundant NOX1, suggesting that NOX1 may stimulate NF-kappaB-dependent antiapoptotic pathways in colon tumours (Fukuyama, M. et al. 2005, Cancer Lett. 221, 97-104).

Wnt3a/beta-Catenin signaling has been described to induce NOX1 expression (Petropoulos, H. & Skerjanc, I. S. 2002, J Biol Chem. 277, 15393-15399).

Recently, reactive oxygen species (ROS) have been suggested to induce endothelial apoptosis that subsequently induces the expression of various adhesion molecules for tumour cells. This indicates that by tackling the production of ROS preventing tumour recurrence at distant sites might be feasible (Ten, K M, et al., 2006, Br. J Cancer.).

Ornithine Decarboxylase 1 (ODC1)

ODC1 is the rate-limiting enzyme of the polyamine biosynthesis pathway that catalyses ornithine to putrescine. The activity level for the enzyme varies in response to growth-promoting stimuli and exhibits a high turnover rate in comparison to other mammalian proteins.

Polyamine metabolism is an integral component of the mechanism of carcinogenesis in epithelial tissues. Increases in ODC1 are often associated with initiation of normal cell growth and with sustained neoplastic cell growth. Inhibitors of ODC1 suppress tumour formation in experimental models of bladder, breast, colon and skin carcinogenesis. Over-expression of ODC1 activity is a well-recognized feature of many cancers and ODC1 has been considered as a proto-oncogene (Auvinen, M., et al., Nature 360, 355-358, 1992).

Germline mutations in the adenomatous polyposis coli (APC) gene are one of the most clearly defined inherited predispositions for colon cancer. APC mutations cause a substantial increase in free β-catenin levels, which moves into the nucleus, where it forms a complex with members of the lymphoid-enhancing factor (LEF)/T-cell factor (Tcf) family of sequence-specific transcription factors. The c-myc oncogene is one of the Tcf target genes. He, T. C. et al. Science 281, 1509-1512 (1998). c-Myc RNA and protein are overexpressed in both early and late stages of colorectal tumorigenesis. ODC is a c-Myc target gene.

Loss of APC function causes an upregulation of ODC1 (Gemer, E W et al., 2004, Nat. Rev. Cancer, 4, 781-792) and overexpression has been frequently observed in colorectal carcinoma (Hu, H. Y. et al. World J. Gastroenterol. 11, 2244-2248 (2005); Kitahara, O. et al. Cancer Res. 61, 3544-3549 (2001); Nemoto, T., et al., World J. Gastroenterol. 11, 3065-3069 (2005)).

ODC1 has pro-angiogenic properties by acting as an endostatin suppressor (Nemoto, T., et al., Blood 99, 1478-1481 (2002)).

Infection of the CRC cell line HT-29 with an adenovirus encoding antisense RNA for ODC1 and S-adenosylmethionine decarboxylase (another important enzyme of the polyamine biosynthesis pathway) leads to a downregulation of CCND1 and cell cycle arrest. Moreover, nuclear translocation of beta-catenin was also inhibited (Gong, L, et al., 2006, J Biochem. Mol. Biol, 39, 730-736). The adenovirus also induced tumor regression in established tumors in nude mice (Zhang, B, Liu, et al., 2006, J Gene Med, 8, 980-989).

A specific and irreversible inhibitor of ODC1 is 2-difluoromethylornithine (DMFO, Eflornithine (Sanofi-Aventis)). It is marketed for the treatment of sleeping sickness (caused by trypanosomes) and is the active ingredient of the hair removal cream Vaniqa®.

With respect to cancer, DMFO has been widely used in pre-clinical models and shown promising anti-tumor effects by decreasing polyamine levels (Gemer, E W et al., 2004, Nat. Rev. Cancer, 4, 781-792). Clinical trials have been performed for several cancers and some are currently underway for CRC. However, these studies are mostly combination approaches performed in preventive settings with patients especially susceptible to CRC (adenomatous polyps). The immunogenic ODC peptide ODC-001 has been identified previously (M. Diehl, PhD Thesis, University of Tübingen, 1998).

Proliferating Cell Nuclear Antigen (PCNA)

PCNA is found in the nucleus and is a cofactor of DNA polymerase delta. The encoded protein acts as a homotrimer and helps increase the processivity of leading strand synthesis during DNA replication. Therefore, it is expressed in all proliferating cells, especially tumour cells, and is used as a marker to detect proliferation.

Proliferation indexes in neoplastic and adjacent normal mucosa, as defined by PCNA immunohistochemical analysis, have long been known as independent predictors of recurrence and poor survival in patients with colorectal cancer (al-Sheneber, IF, et al., 1993, Cancer, 71, 1954-1959; Mayer, A, et al., 1993, Cancer, 71, 2454-2460; Nakamura, T, et al., 1996, Cancer, 77, 1741-1746).

DNA Topoisomerase II (TOP2)

TOP2A and TOP2B encode isoforms of a DNA topoisomerase, an enzyme that controls and alters the topologic states of DNA during transcription. This nuclear enzyme is involved in processes such as chromosome condensation, chromatid separation, and the relief of torsional stress that occurs during DNA transcription and replication. It catalyses the transient breaking and rejoining of two strands of duplex DNA, which allows the strands to pass through one another, thus altering the topology of DNA. The two isoforms of this enzyme exist as likely products of a gene duplication event. The gene encoding the alpha form is localized to chromosome 17 and the beta gene is localized to chromosome 3.

TOP2A is the target for several anticancer agents and a variety of mutations in this gene have been associated with the development of drug resistance.

The TOP2A gene is located adjacent to the HER-2 oncogene, the most frequently amplified oncogene in breast cancer, at the chromosome location 17q12-q21 and is either amplified or deleted, with equal frequency, in almost 90% of HER-2 amplified primary breast tumours (Jarvinen, T A et al., Cytopathology, 14, 309-313, 2003). Furthermore, TOP2A amplifications have been reported for other cancers. Recent experimental as well as numerous, large, multi-center trials suggest that amplification (and/or deletion) of TOP2A may account for both sensitivity or resistance to commonly used cytotoxic drugs, i.e. topoisomerase II inhibitors (anthracyclines etc.) (Kellner, U, et al., 2002, Lancet Oncol., 3, 235-243)), depending on the specific genetic defect at the TOP2A locus (Jarvinen, T A et al., 2006, Curr. Cancer Drug Targets., 6, 579-602).

Without TOP2A, DNA replication and cell division are impossible. It has therefore become the main target of many antitumour therapy regimens, even though the exact mechanism of cell killing remains elusive (Kellner, U, et al., Lancet Oncol., 3, 235-243, 2002). The success of this approach is limited by the development of spontaneous resistance, and drug-induced DNA damage can increase malignancy.

TOP2B, the second potential source protein for TOP-001, has not been in the focus of cancer research because it is located in a chromosomal region (3p24) that is not known for frequent amplification in tumors. However, TOP2B is similar in primary structure to TOP2A and has almost identical catalytic properties (Leontiou, C, et al., 2003, FEBS Lett., 554, 206-210). In another study it has also been shown that both isoforms can substitute for each other (Sakaguchi, A et al., 2004, J Cell Sci., 117, 1047-1054).

Carcinoembryonic Antigen-related Cell Adhesion Molecule 5

Carcinoembryonic antigen (CEA=CEACAM5) is a 180 kDa heavily glycosylated membrane protein composed of three C2 Ig-like repeating units flanked by a N-terminal Ig V-like region and a C-terminal region, which includes glycophosphatidylinositol linkage region (Hegde, P, et al., Cancer Res., 61, 7792-7797, 2001).

As an oncofetal antigen, CEA is expressed during fetal development, but also, at low levels, in the gastrointestinal epithelium of adults. However, CEA is overexpressed in a high percentage of human tumours, including 90% of gastrointestinal, colorectal and pancreatic cancer, 70% of non-small cell lung cancer cells and 50% of breast cancers (Thompson, J A, et al., J Clin Lab Anal., 5, 344-366, 2005). Due to its high expression by tumour cells and its secretion to the serum, CEA has been broadly used as a tumour marker (Sikorska, H, et al., Cancer Detect. Prev., 12, 321-355, 1992) and is the standard serum marker for colorectal cancer monitoring (Locker, G Y, et al., J Clin Oncol, 24, 5313-5327, 2006).

Despite the overexpression of CEA in tumour cells, cancer patients do not normally show an immune response against this antigen (Orefice, S, et al., Tumouri, 68, 473-475, 1982). The immune system commonly becomes tolerant to CEA, because it is normally expressed at low levels in the body. However, in a series of clinical vaccine trials, the immunogenicity of CEA has been demonstrated (Sarobe, P, et al., Curr. Cancer Drug Targets., 4, 443-454, 2004), especially in colorectal carcinoma (CRC) (Mosolits, S, et al., Ann. Oncol., 16, 847-862, 2005), and CEA is the tumour associated antigen (TAA) with the greatest number of vaccine platforms tested in this tumour type (von Mehren, M; Colorectal cancer vaccines: what we know and what we don't yet know, Semin. Oncol., 32, 76-84, 2005).

Several cytotoxic and helper T-cell epitopes have been described for CEA (Crosti, M, et al., J Immunol., 176, 5093-5099, 2006; Novellino, L, et al., Cancer Immunol. Immunother., 54, 187-207, 2005; Ruiz, M, et al., Clin Cancer Res., 10, 2860-2867, 2004), enabling a variety of peptide-based vaccination trials in CRC. (Babatz, J, et al., Cancer Immunol. Immunother., 55, 268-276, 2006; Fong, L, et al.; Proc. Natl. Acad. Sci. U.S.A, 98, 8809-8814, 2001; Liu, K J, et al., Clin Cancer Res., 10, 2645-2651, 2004; Matsuda, K, et al., Immunother., 53, 609-616, 2004; Ueda, Y, et al., Int. J Oncol., 24, 909-917, 2004; Weihrauch, M R, et al., Clin Cancer Res., 11, 5993-6001, 2005). These and other clinical trials to date have demonstrated safety of CEA vaccinations and evidence for the induction of immune response against this antigen (von Mehren, M; et al., Semin. Oncol., 32, 76-84, 2005). A variant of CEA-006 was published previously (Ruiz, M, et al., 2004, Clin Cancer Res., 10, 2860-2867).

Transforming Growth Factor, Beta-Induced (TGFBI)

TGFBI was first identified as a TGF-beta-inducible gene in a human lung adenocarcinoma cell line. It encodes a secreted extracellular matrix protein, which is thought to act on cell attachment and extracellular matrix composition.

TGFBI was shown to be among the most significantly elevated genes in colorectal cancers and it is expressed at high levels in adenomas as well. Quantitative PCR results demonstrated strong elevation in both unpurified tumours and purified tumour epithelial cells. Accordingly, in situ hybridization experiments revealed TGFBI to be expressed in many cell types, in both the stromal and epithelial compartments (Buckhaults, P, et al., Cancer Res., 61, 6996-7001, 2001).

In a meta-analysis of studies investigating gene expression in colorectal carcinoma, TGFBI was identified as one of only nine genes described as upregulated repeatedly (4 studies for TGFBI) (Shih, W, et al., Oncol. Rep., 13, 517-524, 2005).

In human pancreatic tissues, there was a 32.4-fold increase in TGFBI mRNA levels in pancreatic cancers in comparison to normal control tissues. In situ hybridization analysis revealed that TGFBI mRNA was expressed mainly in the cancer cells within the pancreatic tumour mass (Schneider, D, et al., Biochim. Biophys. Acta, 1588, 1-6, 2002).

TGFBI was identified as a gene promoting angiogenesis in an in vitro model. Additionally, dramatically enhanced expression of TGFBI was detected in several tumours. Antisense oligonucleotides to TGFBI blocked both gene expression and endothelial tube formation in vitro, suggesting that TGFBI may play a critical role in endothelial cell-matrix interactions (Aitkenhead, M, et al., Microvasc. Res., 63, 159-171, 2002).

Mucin-1 (MUC1)

Mucins are high-molecular weight epithelial glycoproteins with a high content of clustered oligosaccharides O-glycosidically linked to tandem repeat peptides rich in threonine, serine, and proline. There are two structurally and functionally distinct classes of mucins: transmembrane mucins, to which MUC1 belongs, and secreted gel-forming mucins. Colon cancer mucins have differences in carbohydrate structures that are being investigated as diagnostic and prognostic markers, and also as targets for cancer vaccines.

The extracellular domain of the MUC 1 protein is made up of highly conserved repeats of 20 amino acids, the actual number varying between 25 and 100 depending on the allele. Each tandem repeat contains five potential glycosylation sites, and between doublets of threonines and serines lies an immunodominant region, containing epitopes recognized by various anti-MUC1 antibodies (Taylor-Papadimitriou, et al., 1999, Biochim. Biophys. Acta, 1455, 301-313).

Compared to most other epithelia, the MUC1 of colon is more heavily glycosylated thereby masking the MUC1 protein for immunohistochemical staining by MUC1-specific antibodies. In colorectal adenocarcinomas, MUC1 is less glycosylated, allowing immunodetection. The aberrantly glycosylated MUC1 confers new binding properties and can simultaneously mediate and block binding to adhesion molecules with some molecular specificity, thereby playing a dual role in the metastatic spread of tumor cells (McDermott, K M, et al., 2001, Int. J Cancer, 94, 783-791).

MUC1 as detected immunologically is increased in expression in colon cancers, which correlates with a worse prognosis (Byrd, J C et al., 2004, Cancer Metastasis Rev., 23, 77-99), indicating that upregulation of MUC1 may be involved in the progression of CRC. Colon cancers with metastasis express MUC1 more strongly than those without metastasis (Nakamori, S, et al., 1994, Gastroenterology, 106, 353-361), and MUC1 staining was positive in all colorectal cancers with hepatic involvement in one study (Matsuda, K, et al., 2000, Jpn. J Clin Oncol., 30, 89-94). A recent study in 462 colorectal cancer patients found MUC1 expression to be an independent prognostic marker of poor prognosis (Duncan, T J, et al., 2007, World J Surg. Oncol, 5, 31-).

There is a pathophysiological significance of circulating anti-MUC1 antibodies in CRC: anti-MUC1 antibodies were detected in 5 of 31 (16.1%) healthy subjects and in 27 of 56 (48.2%) patients with colorectal cancer (Nakamura, H, et al., 1998, J Gastroenterol., 33, 354-361).

Apart from its role as an antibody target, MUC1 is also a well-established target for cytotoxic T cells. Several reports demonstrated that cytotoxic MHC-unrestricted T cells from ovarian, breast, pancreatic, and multiple myeloma tumors can recognize epitopes of the MUC1 protein core localized in the tandem repeat (Apostolopoulos, V., et al., 1994, Crit Rev. Immunol., 14, 293-309; Finn, O J, et al., 1995, Immunol. Rev., 145, 61-89; Barnd, D L, et al., 1989, Proc. Natl. Acad. Sci. U.S.A, 86, 7159-7163; Takahashi, T, et al., 1994, J. Immunol., 153, 2102-2109; Noto, H, et al., 1997, Int. Immunol., 9, 791-798). However, HLA-A*02 restricted T cell epitopes derived from the MUC1 protein have also been identified (Apostolopoulos, V, et al., 1997, J Immunol., 159, 5211-5218; Brossart, P, et al., 1999, Blood, 93, 4309-4317). One of those peptides is MUC-001. It is derived from the tandem repeat region of the MUC1 protein. Induction of cytotoxic T-lymphocyte responses in vivo after vaccinations with peptide-pulsed dendritic cells in patients with advanced breast or ovarian cancer using these MUC1 peptides has been successful (Brossart, P, et al., 2000, Blood, 96, 3102-3108; Wierecky, J, et al., 2005, Apr. 28:288-94). Moreover, such vaccinations have successfully induced clinical responses in renal cell carcinoma patients (Wierecky, J, et al, 2006, Cancer Res., 66, 5910-5918).

Upregulation of immunoreactive MUC1 in colorectal cancer is mostly not based on mRNA overexpression, but rather caused by its decreased glycosylation, which unmasks epitopes for antibody recognition, especially in the tandem repeat region of MUC1. This deglycosylation provides at the same time an opportunity for the generation of T cell epitopes by altered antigen processing in tumor cells, which is prevented in normal cells by glycosylation. This mechanism may explain the striking features of MUC-00 1 as a tumor associated T cell epitope despite the absence of strong mRNA overexpression. Some evidence that glycosylation changes may indeed affect antigen processing comes from a recent observation that altered glycosylation of MUC1 in colorectal cancer can be actually detected by antigen presenting cells via a receptor specifically recognizing tumor glycoforms (Saeland, E, et al., Cancer Immunol. Immunother., 2007, 56(8): 1225-36). A specific uptake and processing of tumor glycoforms by antigen presenting cells may also explain the fact that MUC-001 specific T cells have been observed naturally (without immunization) in breast (Rentzsch, C, et al., 2003, Clin Cancer Res., 9, 4376-4386) and colorectal cancer patients (Dittmann, J, et al., 2005, Cancer Immunol. Immunother., 54, 750-758). In these patients no autoimmune effects were reported. This demonstrates the natural role of MUC-001 as a tumor associated peptide inducing specific T cells and suggests that the administration of MUC-001 can be considered safe although no overexpression can be detected for the MUC1 antigen at the mRNA level.

Met Proto-oncogene (Hepatocyte Growth Factor Receptor) (c-Met)

The MET proto-oncogene protein product is the hepatocyte growth factor receptor. It contains a tyrosine kinase domain that activates signaling pathways involved in cell proliferation, motility, adhesion, and invasion (Trusolino, L., et al., 2002, Nat. Rev. Cancer, 2, 289-300).

Studies in various tumor types have demonstrated several mechanisms for c-Met activation, including HGF/c-Met autocrine loop, activating point mutations, TPR-Met fusion protein, and failure to cleave c-Met into the α and β chains (Di Renzo, MF, et al., 2000, Oncogene, 19, 1547-1555; Ebert, M, et al., 1994, Cancer Res., 54, 5775-5778; Mondino, A, et al., 1991, Mol. Cell Biol., 11, 6084-6092; Olivero, M, et al., 1999, Int. J Cancer, 82, 640-643; Park, M, et al., 1986, Cell, 45, 895-904; Park, W S, et al., 1999, Cancer Res., 59, 307-310; Rahimi, N, et al., 1996, Cell Growth Differ., 7, 263-270; Schmidt, L, et al., 1997, Nat. Genet., 16, 68-73; Schmidt, L, et al., 1998, Cancer Res., 58, 1719-1722). Mechanistically, c-Met overexpression cooperates with oncogenic Ki-ras mutation to enhance tumorigenicity of colon cancer cells in vivo (Long, I S, et al., 2003, Mol. Cancer Res., 1, 393-401).

Interestingly, there is some evidence for interactions of MET signalling with the Wnt/beta-catenin pathway frequently upregulated in colon cancer. MET can be activated by Prostaglandin E2 (PGE2), and PGE2-activated c-Met associates with β-catenin and increases its tyrosine phosphorylation thereby inducing colon cancer cell invasiveness (Pai, R, et al., 2003, FASEB J, 17, 1640-1647). Recently, mutual activation of MET and beta-catenin has been described, resulting in a positive feedback loop between these two key players in colorectal tumorigenesis (Rasola, A, et al., 2007, Oncogene, 26, 1078-1087).

The c-Met mRNA expression level in primary CRC tumors (n =36) is an important predicitive marker for early-stage invasion and regional disease metastasis, thus correlating directly with colon cancer stage (Takeuchi, H, et al., 2003, Clin Cancer Res., 9, 1480-1488). Another analysis of c-Met expression of 130 CRC samples showed overexpression (T/N>2.0) of c-Met in 69% primary CRC and significantly higher c-Met levels in CRC with blood vessel invasion (P=0.04), and in advanced stage (P=0.04) supporting the role for c-Met in human CRC progression and metastasis (Zeng, Z, et al., 2004, Clin Exp. Metastasis, 21, 409-417). In another study 69% and 48% of 60 colon adenocarcinomas showed a greater than 2-and greater than 10-fold elevation in c-Met mRNA, respectively, compared to adjacent normal mucosa (Kammula, U S, et al., 2007, Cancer Lett., 248, 219-228). Thus, increased c-Met signalling is a common occurrence in early stage CRC, but with even greater expression occurring in advanced and metastatic disease.

Cyclin D1 (CCND1)

CCND1 belongs to the highly conserved cyclin family, whose members are characterized by a dramatic periodicity in protein abundance throughout the cell cycle. Cyclins function as regulators of CDK kinases. Different cyclins exhibit distinct expression and degradation patterns, which contribute to the temporal coordination of each mitotic event. This cyclin forms a complex with and functions as a regulatory subunit of CDK4 or CDK6, whose activity are required for cell cycle G1/S transition. Mutations, amplification and overexpression of this gene, which alters cell cycle progression, are observed frequently in a variety of tumors and may contribute to tumorigenesis (Fu, M, et al., 2004, Endocrinology, 145, 5439-5447).

A common A/G single nucleotide polymorphism (A870G) results in two distinct mRNA isoforms a and b. The alternately spliced isoform b encodes a truncated protein that has been linked to higher incidence of tumor onset including lung cancer, colon cancer, and other cancer types (Fu, M, Wang, et al., 2004 Endocrinology, 145, 5439-5447).

For colorectal cancer, overexpression of CCND1 at the mRNA and protein levels has been frequently described (Sutter, T, et al., 1997, J Med, 28, 285-309; Mermelshtein, A, et al., 2005 Br. J Cancer, 93, 338-345; Balcerczak, E, et al., 2005, Eur. J Surg. Oncol., 31, 721-726; Bondi, J, et al., 2005, J Clin Pathol., 58, 509-514; Perez, R, et al., 2003, Gastrointest. Surg., 7, 884-889; Wong, N A, et al., 2002, J Pathol., 197, 128-135; McKay, J A, et al., 2000 Int. J Cancer, 88, 77-81; Bartkova, J, et al., 1994, Int. J Cancer, 58, 568-573).

This can be explained by the well-established fact that CCND1 is a target gene of the β-Catenin-TCF/LEF pathway, which is frequently upregulated in colorectal carcinoma (Shtutman, M, et al., 1999, Proc. Natl. Acad. Sci. U.S.A, 96, 5522-5527; Tetsu, O, et al., 1999, Nature, 398, 422-426).

Enhanced CCND1 expression has been linked to higher tumor grades, metastasis, and decreased survival (Balcerczak, E, et al., 2005, Eur. J Surg. Oncol., 31, 721-726; Bahnassy, A A, et al., 2004, BMC. Gastroenterol., 4, 22; McKay, J A, et al., 2000, Int. J Cancer, 88, 77-81; Maeda, K, et al, 1998, Oncology, 55, 145-151).

Matrix Metallopeptidase 7 (Matrilysin, Uterine) (MMP7)

Matrix metalloproteinases (MMPs) are a large family of structurally related zinc-dependent proteinases typically described as capable of degrading components of the extracellular matrix. Individual MMPs have been identified that show increased expression in tumors and most tumors show enhanced MMP activity (Curran, S and Murray, G I; 1999, Matrix metalloproteinases in tumour invasion and metastasis, J Pathol., 189, 300-308; Curran, S and Murray, G I; 2000, Matrix metalloproteinases: molecular aspects of their roles in tumour invasion and metastasis, Eur. J Cancer, 36, 1621-1630).

Basal membrane and extracellular matrix represent two physical barriers to malignant invasion, and their degradation by MMPs plays a key role in tumor progression and metastatic spread (Johnsen, M, et al., 1998, Curr. Opin. Cell Biol., 10, 667-671; Nelson, A R, et al, 2000, J Clin Oncol., 18, 1135-1149; Wang, F Q, et al., 2005, Int. J Cancer, 114, 19-31). Apart from this function, MMPs are now discussed for their involvement in tumour development and progression including roles in apoptosis, cell proliferation, and cell differentiation. These functions are linked to MMP-mediated proteolysis of non-matrix proteins and actions distinct from their enzyme activity (Egeblad, M and Werb, Z; 2002, Nat. Rev. Cancer, 2, 161-174; Leeman, M F, et al., 2003, J. Pathol., 201, 528-534).

Recent studies have shown that several matrix metalloproteinases, especially matrilysin (MMP7), interact with the specific molecular genetic and signalling pathways involved in colorectal cancer development. In particular, matrilysin is activated at an early stage of colorectal tumourigenesis by the beta-catenin signalling pathway (Brablez, T, et al., 1999, Am. J Pathol., 155, 1033-1038; Leeman, M F, et al., 2003, J. Pathol., 201, 528-534; Zucker, S and Vacirca, J, 2004, Cancer Metastasis Rev., 23, 101-117).

MMP7 is overexpressed both in benign and malignant colorectal tumors (Ishikawa, T, et al., 1996, Cancer Lett., 107, 5-10; McDonnell, S, et al., 1991, Mol. Carcinog., 4, 527-533; Miyazaki, K, et al., 1990, Cancer Res., 50, 7758-7764; Nagashima, Y, et al., 1997, Int. J Cancer, 72, 441-445; Newell, K J, et al., 1994, Mol. Carcinog., 10, 199-206; Yoshimoto, M, et al., 1993, Int. J Cancer, 54, 614-618). MMP7 is one of only a few MMPs that is actually secreted by tumour cells (Overall, C M and Kleifeld, O; 2006, Nat. Rev. Cancer, 6, 227-239). Furthermore, the levels of MMP7 mRNA expression correlate with the stage of CRC progression (Ishikawa, T, et al., 1996, Cancer Lett., 107, 5-10; Mori, M, et al., 1995, Cancer, 75, 1516-1519). In CRC metastases, MMP7 plays also a critical role (Adachi, Y, et al., 1999, Gut, 45, 252-258; Mori, M, et al., 1995, Cancer, 75, 1516-1519).

Elevated MMP7 serum levels are associated with a poor prognosis in advanced colorectal cancer patients (Maurel, J, et al., 2007, Int. J Cancer, Published Online: 8 May 2007) and overexpression in CRC patients, associated again with decreased survival, has been suggested to promote escape from immune surveillance by cleaving Fas on tumor cells (Wang, W S, et al., 2006, 27, 1113-1120).

In the present invention the inventors provide conclusive evidence that tumour-associated peptides sufficiently binding to HLA-class I molecules are able to elicit immune responses mediated by human CD8-positive cytotoxic T-lymphocytes, also demonstrating that the claimed peptides are suitable for triggering responses of the human immune system against selected peptides of the tumour cell peptidome.

Similarly, it was found that tumour-associated peptides sufficiently binding to HLA-class II molecules, especially those HLA class II alleles genetically encoded by HLA DR loci of the human genome, are able to elicit immune responses mediated by human CD4-positive T-cells. CD4-positive T-cells were isolated from human peripheral blood, demonstrating that the claimed peptides are suitable for triggering T-cell responses of the human immune system against selected peptides of the tumour cell peptidome. As exemplified below with a peptide TGFBI-004, this HLA-DR-binding, tumour-associated peptide was found to be recognized by CD4-positive T-cells.

As peptides can be synthesized chemically and can be used as active pharmaceutical ingredients of pharmaceutical preparations, the peptides provided by the present invention can be used for immunotherapy, preferentially cancer immunotherapy.

In another aspect the pharmaceutical composition further comprises at least one additional peptide containing an amino acid sequence selected from the group consisting of SEQ ID NO: 8 to SEQ ID NO: 15, or containing a variant amino acid sequence that is at least 80% homologous to that of SEQ ID NO: 8 to SEQ ID NO: 15, or a polynucleotide containing a nucleic acid encoding SEQ ID NO: 8 to SEQ ID NO: 15 or the variant amino acid sequence.

The peptides of SEQ ID NO: 8 to SEQ ID NO: 13 and 15 are immunogenic peptides previously identified and bind to MHC class I and MHC class II molecules (see Table 2).

These peptides were shown to elicit T-cell responses in vivo in patients suffering from renal cell carcinoma (RCC) (H. Singh-Jasuja, et al., ASCO Meeting 2007 Poster # 3017; M. Staehler, et al., ASCO meeting 2007; Poster # 3017). Since the parent proteins are not only overexpressed in RCC but also CRC and other types of cancer these peptides are also useful in vaccines for the treatment of other tumour types, in particular antiCRC vaccines.

TABLE 2

Additional immunogenic peptides useful in a composition of the invention

| SEQ ID NO: | Peptide ID | Sequence | Gene Symbol | Function | binds to MHC |
|---|---|---|---|---|---|
| 8 | CEA-006 | SPQYSWRINGIPQQHT | CEACAM5 | Carcinoembryonic antigen | HLA-DR |
| 9 | CCN-001 | LLGATCMFV | CCND1 | Cyclin D1 | HLA-A*02 |
| 10 | MUC-001 | STAPPVHNV | MUC1 | Mucin 1 | HLA-A*02 |

TABLE 2-continued

Additional immunogenic peptides useful
in a composition of the invention

| SEQ ID NO: | Peptide ID | Sequence | Gene Symbol | Function | binds to MHC |
|---|---|---|---|---|---|
| 11 | MMP-001 | SQDDIKGIQKLYGKRS | MMP7 | Metalloproteinase 7 | HLA-DR |
| 12 | CEA-005 | YLSGADLNL | CEACAM5 | variant of CEA peptide | HLA-A*02 |
| 13 | MET-001 | YVDPVITSI | MET | met proto-oncogene | HLA-A*02 |
| 14 | (HBV-001) | FLPSDFFPSV | | control peptide | |
| 15 | CEA-004 | YLSGANLNL | CEACAM5 | CEA peptide | HLA-A*02 |

The proteins of the invention can be the target of a tumour specific immune response in multiple types of cancer.

The Hepatitis B Virus Core Antigen peptide HBV-001 is not derived from an endogenous human tumour-associated antigen, but is derived from the Hepatitis B virus core antigen. First, it allows quantitative comparisons of the magnitude of T-cell responses induced by TUMAPs and hence allows important conclusions on the capacity to elicit anti-tumour responses. Second, it functions as an important positive control if there is no T-cell responses in the patient. Third, it also allows conclusions on the status of immunocompetence of the patient.

Hepatitiv B virus (HBV) infection is among the leading causes of liver disease, affecting approximately 350 million people world-wide (Rehermann, B and Nascimbeni, M; 2005, Nat. Rev. Immunol., 5, 215-229). Due to the ease of horizontal and vertical transmission and the potential for chronic disease that may lead to liver cirrhosis and hepatocellular carcinoma, HBV represents a major impact on the public health system for many countries worldwide. The HBV genome (Previsani, N and Lavanchy, D; 2002, Hepatitis B, (Epidemic and Pandemic Alert and Response, World Health Organization, Geneva, 2002)) is comprised of partially double-stranded circular DNA. In HBV virions, it is packed together with the core protein HBc and other proteins to form the nucleocapsid, which is surrounded by an outer envelope containing lipids and the surface protein family HBs (also called envelope protein). The antigenic determinants that are associated with HBc and HBs are noted as HBcAg and HBsAg, respectively. These antigens are associated with serological, i.e. antibody responses found in the patient blood and are among the clinically most useful antigen-antibody systems for the diagnosis of HBV infection. HBc will represent a novel foreign antigen for all individuals without prior history of HBV infection. As immunogenic peptides are well known for this antigen (Bertoletti, A, et al., 1993, J. Virol., 67, 2376-2380; Livingston, B D, et al., 1997, J. Immunol., 159, 1383-1392), one ten-amino acid peptide from HBcAg was selected as a positive control antigen within IMA. The induction of HBc peptide-specific CTLs will then be used as a marker for patient immunocompetence and successful vaccination.

In another embodiment a peptide from another viral antigen may be used as a control marker.

The pharmaceutical composition can furthermore contain additional peptides and/or excipients to be more effective, as will be further explained below.

By a "variant amino acid sequence" of the given amino acid sequence the inventors mean that the side chains of, for example, one or two of the amino acid residues are altered (for example by replacing them with the side chain of another naturally occurring amino acid residue or some other side chain) so that the peptide is still able to bind to an HLA molecule in substantially the same way as a peptide consisting of the given amino acid sequence. For example, a peptide may be modified so that it at least maintains, if not improves, the ability to interact with and bind a suitable MHC molecule, such as HLA-A or -DR, and so that it at least maintains, if not improves, the ability to generate activated CTL, which can recognize and kill cells that express a polypeptide containing an amino acid sequence as defined in the aspects of the invention. As can be derived from the database, certain positions of HLA-A binding peptides are typically anchor residues forming a core sequence fitting to the binding motif of the HLA binding groove.

Those amino acid residues that are not essential to interact with the T-cell receptor can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide) that includes the amino acid sequences or a portion or variant thereof as given.

It is furthermore known for MHC-class II presented peptides that these peptides are composed of a "core sequence" having a certain HLA-specific amino acid motif and, optionally, N- and/or C-terminal extensions that do not interfere with the function of the core sequence (i.e. are deemed as irrelevant for the interaction of the peptide and the T-cell). The N- and/or C-terminal extensions can, for example, be between 1 to 10 amino acids in length, respectively. These peptides can be used either directly to load MHC class II molecules or the sequence can be cloned into the vectors according to the description herein below. As these peptides form the final product of the processing of larger peptides within the cell, longer peptides can be used as well. The peptides of the invention may be of any size, but typically they may be less than 100,000 in molecular weight, preferably less than 50,000, more preferably less than 10,000 and typically about 5,000. In terms of the number of amino acid residues, the peptides of the invention may have fewer than 1000 residues, preferably fewer than 500 residues, more preferably fewer than 100 residues. Accordingly the present invention provides also compositions of peptides and variants thereof wherein the peptide or variant has an overall length of between 8 and 100, preferably between 8 and 30, and most preferred between 8 and 16, namely 8, 9, 10, 11, 12, 13, 14, 15, or 16 amino acids.

Correspondingly, variants that induce T-cells cross-reacting with a peptide of the invention are often length variants.

If a peptide longer than around 12 amino acid residues is used directly to bind to a MHC class II molecule, it is preferred that the residues that flank the core HLA binding region do not substantially affect the ability of the peptide to bind specifically to the binding groove of the MHC class II molecule or to present the peptide to the CTL. However, as already indicated above, it will be appreciated that larger peptides may be used, especially when encoded by a polynucleotide, since these larger peptides may be fragmented by suitable antigen-presenting cells.

It is also possible, that MHC class I epitopes, although usually between 8-10 amino acids long, are generated by peptide processing from longer peptides or proteins that include the actual epitope. Similar to MHC class II epitopes, it is preferred that the residues flanking the binding region do not substantially affect the ability of the peptide to bind specifically to the binding groove of the MHC class I molecule or to present the peptide to the CTL, nor mask the sites for proteolytic cleavage necessary to expose the actual epitope during processing.

Accordingly the present invention also provides peptides and variants of MHC class I epitopes wherein the peptide or variant has an overall length of between 8 and 100, preferably between 8 and 30, and most preferred between 8 and 16, namely 8, 9, 10, 11, 12, 13, 14, 15, or 16 amino acids.

Of course, the peptide or variant according to the present invention will have the ability to bind to a molecule of the human major histocompatibility complex (MHC) class I or II. Binding of a peptide or a variant to a MHC complex may be tested by methods known in the art, for example those described in the examples of the present invention below or those described in the literature for different MHC class II alleles (e.g. Vogt A B, et al., J Immunol. 1994; 153(4):1665-1673; Malcherek G, et al., J Immunol. 1994; 153(3):1141-1149; Manici S, et al., J Exp Med. 1999; 189(5): 871-876; Hammer J, et al., J Exp Med. 1995 181(5):1847-1855; Tompkins S M, et al., J Immunol Methods. 1993; 163(2): 209-216; Boyton R J, et al., Int Immunol. 1998 (12):1765-1776).

Additional N- and/or C-terminally located stretches of amino acids that do not necessarily formi part of the peptide that functions as an epitope for MHC molecules but may, nevertheless, be important to provide an efficient introduction of the peptide into the cells. In one embodiment of the present invention, the peptide of the present invention is a fusion protein that comprises, for example, the 80 N-terminal amino acids of the HLA-DR antigen-associated invariant chain (p33, in the following "Ii") as derived from the NCBI, GenBank Accession-number X00497 (Strubin, M., et al., EMBO J. 3 (4), 869-872 (1984)).

The present invention further provides a preferred pharmaceutical composition, wherein the peptides have an overall length of between 8 and 100, preferably between 8 and 30, and most preferred between 8 and 16 amino acids.

In addition, the peptide or variant may be modified further to improve stability and/or binding to MHC molecules to elicit a stronger immune response. Methods for such an optimization of a peptide sequence are well known in the art and include, for example, the introduction of reverse peptide bonds or non-peptide bonds. Thus, according to another aspect the invention provides a pharmaceutical composition, wherein the at least one peptide or variant includes non-peptide bonds.

In a reverse peptide bond, amino acid residues are not joined by peptide (—CO—NH—) linkages but the peptide bond is reversed. Such retro-inverso peptidomimetics may be made using methods known in the art, for example such as those described in Meziere et al. (1997) J. Immunol. 159, 3230-3237, incorporated herein by reference. This approach involves making pseudopeptides containing changes involving the backbone, and not the orientation of side chains. Meziere et al. (1997) show that for MHC and T helper cell responses, these pseudopeptides are useful. Retro-inverse peptides containing NH—CO bonds instead of CO—NH peptide bonds, are much more resistant to proteolysis.

A non-peptide bond is, for example, —$CH_2$—NH, —$CH_2$S—, —$CH_2CH_2$—, —CH=CH—, —$COCH_2$—, —CH(OH)$CH_2$—, and —$CH_2$SO—. U.S. Pat. No. 4,897,445 provides a method for the solid phase synthesis of non-peptide bonds (—$CH_2$—NH) in polypeptide chains that involves polypeptides synthesized by standard procedures and the non-peptide bond synthesized by reacting an amino aldehyde and an amino acid in the presence of $NaCNBH_3$.

Peptides comprising the sequences of the invention described above may be synthesized with additional chemical groups present at their amino and/or carboxy termini, to enhance, for example, the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, e.g. the hydrophobic group, t-butyloxycarbonyl, or an amido group may be added to the peptides' carboxy termini.

Further, all peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2005, which is incorporated herein by reference. Chemical modification of amino acids includes, but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, Chapter 15 of Current Protocols In Protein Science, Eds. Coligan et al. (John Wiley & Sons NY 1995-2000) provides a more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of Pierce Chemical Company, Sigma-Aldrich and others provide information on specific reagents.

Selective reduction of disulfide bonds in proteins is also common. Disulfide bonds can be formed and oxidized during the heat treatment of biopharmaceuticals.

Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue.

Diethylpyrocarbonate is a reagent for the modification of histidyl residues in proteins. Histidine can also be modified using 4-hydroxy-2-nonenal.

The reaction of lysine residues and other a-amino groups is, for example, useful in binding of peptides to surfaces or the cross-linking of proteins/peptides. Lysine is the site of attachment of poly(ethylene)glycol and the major site of modification in the glycation of proteins.

Methionine residues in proteins can be modified with e.g. iodoacetamide, bromoethylamine, chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethyleneglycol diacrylate and formaldehyde is used for the preparation of hydrogels. Chemical modification of allergens for immunotherapy is often achieved by carbamylation with potassium cyanate.

Generally, peptides and variants (at least those containing peptide linkages between amino acid residues) may be synthesized e.g. using the Fmoc-polyamide mode of solid-phase peptide synthesis as disclosed by Lu et al. (1981) J. Org. Chem. 46, 3433 and references therein.

Purification may be effected by any one, or a combination of, techniques such as recrystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (e.g. polynucleotide) encoding a peptide or variant of the invention. The polynucleotide may be e.g. DNA, cDNA, PNA, CNA, RNA, either single- and/or double-stranded, or native or stabilized forms of polynucleotides, such as e.g. polynucleotides with a phosphorothiate backbone, or combinations thereof and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention. Expression vectors for different cell types are well known in the art and can be selected without undue experimentation.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques.

Guidance can be found e.g. in Sambrook et al. (1989) Molecular Cloning, A Laboratory Manual, Cold Spring Harbor Laboratory, Cold Spring Harbor, N.Y.

In a particularly preferred embodiment of the invention, however, the pharmaceutical composition comprises at least two peptides consisting of amino acid sequences according to SEQ ID NO: 1 to SEQ ID NO: 15. In an even more preferred embodiment of the invention the composition comprises at least 5 peptides consisting of amino acid sequences according to SEQ ID NO: 1 to SEQ ID NO: 15, in an even more preferred embodiment of the invention the composition comprises at least 7 peptides consisting of amino acid sequences according to SEQ ID NO: 1 to SEQ ID NO: 15, in an even more preferred embodiment of the invention the composition comprises at least 10 peptides consisting of amino acid sequences according to SEQ ID NO: 1 to SEQ ID NO: 15, in an equally preferred embodiment of the invention the composition comprises at least 14 peptides consisting of amino acid sequences according to SEQ ID NO: 1 to SEQ ID NO: 15, in the most preferred embodiment of the invention the composition comprises at least 13 peptides consisting of amino acid sequences according to SEQ ID NO: 1 to SEQ ID NO: 15.

The optimum amount of each peptide to be included in the vaccine and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. For example, doses of between 1 and 500 mg 50 µg and 1.5 mg, preferably 125 µg to 500 µg, of peptide or DNA may be given and will depend from the respective peptide or DNA. Doses of this range were successfully used in previous trials (Brunsvig P F, et al., Cancer Immunol Immunother. 2006; 55(12):1553-1564; M. Staehler, et al., ASCO meeting 2007; Abstract No 3017).

The inventive pharmaceutical composition may be compiled so that the selection, number and/or amount of peptides present in the composition is/are tissue, cancer, and/or patient-specific. For instance, the exact selection of peptides can be guided by expression patterns of the parent proteins in a given tissue to avoid side effects. The selection may be dependent on the specific type of cancer, the status of the disease, earlier treatment regimens, the immune status of the patient, and, of course, the HLA-haplotype of the patient. Furthermore, the vaccine according to the invention can contain individualized components, according to personal needs of the particular patient. Examples include varying the amounts of peptides according to the expression of the related TAAs in the particular patient, unwanted side-effects due to personal allergies or other treatments, and adjustments for secondary treatments following a first round or scheme of treatment.

For a composition to be used as a vaccine for CRC, for example, peptides whose parent proteins are expressed in high amounts in normal tissues will be avoided or be present in low amounts in the composition of the invention. On the other hand, if it is known that the tumour of a patient expresses high amounts of a certain protein, the respective pharmaceutical composition for treatment of this cancer may be present in high amounts and/or more than one peptide specific for this particularly protein or pathway of this protein may be included.

A person skilled in the art will be able to select preferred combinations of immunogenic peptides by testing, for example, the generation of T-cells in vitro as well as their efficiency and overall presence, the proliferation, affinity and expansion of certain T-cells for certain peptides, and the functionality of the T-cells, e.g. by analyzing the IFN-y production (see also examples below). Usually, the most efficient peptides are then combined as a vaccine for the purposes as described above.

A suitable vaccine will preferably contain between 1 and 20 peptides, more preferably 2, 3, 4, 5, 6, 7, 8, 9, 10, 11, 12, 13, 14, 15, 16, 17, 18, 19, or 20 different peptides, further preferred 6, 7, 8, 9, 10 11, 12, 13, or 14 different peptides, and most preferably 12, 13 or 14 different peptides. The length of the peptide for use in a cancer vaccine may be any suitable peptide. In particular, it may be a suitable 9-mer peptide or a suitable 7-mer or 8-mer or 10-mer or 11-mer peptide or 12-mer, 13-mer, 14-mer or 15-mer. Longer peptides may also be suitable, 9-mer or 10-mer peptides as described in the attached Tables 1 and 2 are preferred for MHC class I-peptides, while 12- to 15-mers are preferred for MHC class II peptides.

Preferably when the peptides of the invention are used in a vaccine or medicament of the invention, they are present as a salt, such as for example, but not limited to an acetate salt or a chloride salt. Example 6 provides studies of a vaccine IMA-910, containing some of the peptides of the present invention and describes the preparation of the vaccine using peptides in their salt form and their particle size.

Tumor/cancer vaccines of the present invention may be administered directly into the patient, into the affected organ or systemically, or applied ex vivo to cells derived from the patient or a human cell line, which are subsequently administered to the patient, or used in vitro to select a subpopulation from immune cells derived from the patient, which are then re-administered to the patient.

The peptide may be substantially pure, or combined with an immune-stimulating adjuvant (see below) or used in combination with immune-stimulatory cytokines, or administered with a suitable delivery system, for example liposomes. The peptide may also be conjugated to a suitable carrier such as keyhole limpet haemocyanin (KLH) or mannan (see WO 95/18145 and Longenecker et al. (1993) Ann. NY Acad. Sci. 690,276-291). The peptide may also be tagged, or be a fusion protein, or be a hybrid molecule. The peptides whose sequence is given in the present invention are expected to stimulate CD4 or CD8 CTL. However, stimulation is more efficient in the presence of stimulated T-cells positive for the opposite CD. Thus, for MHC Class II epitopes that stimulate CD4 CTL, the fusion partner or sections of a hybrid molecule suitably provide epitopes that stimulate CD8-positive T-cells. On the other hand, for MHC Class I epitopes that stimulate CD8 CTL, the fusion partner or sections of a hybrid molecule suitably provide epitopes that stimulate CD4-positive T-cells. CD4- and CD8-stimulating epitopes are well known in the art and include those identified in the present invention.

To elicit an immune response it is usually necessary to include excipients that render the composition more immunogenic. Thus, in a preferred embodiment of the invention the pharmaceutical composition further comprises at least one suitable adjuvant.

Adjuvants are substances that non-specifically enhance or potentiate the immune response (e.g., immune responses mediated by CTLs and helper-T (TH) cells to an antigen, and would thus be considered useful in the medicament of the present invention. Suitable adjuvants include, but are not limited to 1018 ISS, aluminium salts, Amplivax, AS15, BCG, CP-870,893, CpG7909, CyaA, dSLIM, GM-CSF, IC30, IC31, Imiquimod, ImuFact IMP321, IS Patch, ISS, ISCO-MATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel® vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietory adjuvants such as Ribi's Detox. Quil or Superfos. Adjuvants such as incomplete Freund's or GM-CSF are preferred. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11). Also cytokines may be used. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly, it enhances dendritic cell maturation and differentiation, resulting in enhanced activation of $T_{H1}$ cells and strong cytotoxic T-lymphocyte (CTL) generation, even in the absence of CD4 T-cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Nature Reviews, Drug Discovery, 5, Jun. 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, GERMANY), which is a preferred component of the pharmaceutical composition of the present invention. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly (I:C)(e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives useful in the context of the present invention can readily be determined by the skilled artisan without undue experimentation. Preferred adjuvants are dSLIM, BCG, OK432, imiquimod, PeviTer, and JuvImmune. In a preferred embodiment, pharmaceutical compositions according to the invention include a adjuvant selected from the group consisting of colony-stimulating factors, such as Granulocyte Macrophage Colony Stimulating Factor (GM-CSF, sargramostim).

In a preferred embodiment pharmaceutical compositions of the present invention further comprises the adjuvant imiquimod.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavours, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, 3. Ed. 2000, American Pharmaceutical Association and pharmaceutical press. The composition can be used for a prevention, prophylaxis and/or therapy of adenomateous or cancerous diseases, preferably CRC.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in a preferred embodiment the pharmaceutical composition according to the present invention additionally contains at least one antigen presenting cell.

The antigen-presenting cell (or stimulator cell) typically has an MHC class I or II molecule on its surface, and in one embodiment is substantially incapable of itself loading the MHC class I or II molecule with the selected antigen. As is described in more detail below, the MHC class I or II molecule may readily be loaded with the selected antigen in vitro.

Preferably the mammalian cell lacks or has a reduced level or has reduced function of the TAP peptide transporter. TAP is the Transporter Associated with antigen Processing. Suitable cells that lack the TAP peptide transporter include T2, RMA-S and Drosophila cells. The human peptide loading deficient cell line T2 is available from the American Type Culture Collection, 12301 Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Karre and Ljunggren (1985) J. Exp. Med. 162, 1745. These cell lines can be used as APCs, and due to the lack of TAP nearly all peptides presented by MHC class I will be the peptides under scrutiny used for externally loading the empty MHC class I molecules of these cell lines, hence all effects will clearly be attributable to the peptides of the present invention.

Preferably, the antigen presenting cells are dendritic cells. Suitably, the dendritic cells are autologous dendritic cells that are pulsed with an antigenic peptide. The antigenic peptide may be any suitable antigenic peptide that gives rise to an appropriate T-cell response. T-cell therapy using autologous dendritic cells pulsed with peptides from a tumour associated antigen is disclosed in Murphy et al. (1996) The Prostate 29, 371-380 and Tjua et al. (1997) The Prostate 32, 272-278.

Thus, in a preferred embodiment of the present invention the pharmaceutical composition containing at least one antigen presenting cell is pulsed or loaded with a peptide of the present invention. See example 4.

As an alternative the antigen presenting cell comprises an expression construct encoding a peptide of the present invention. The polynucleotide may be any suitable polynucleotide and it is preferred that it is capable of transducing the dendritic cell, thus resulting in the presentation of a peptide and induction of immunity.

A nucleic acid of the invention may be comprised in a viral polynucleotide or virus. For example, adenovirus-transduced dendritic cells have been shown to induce antigen-specific antitumour immunity in relation to MUC1 (see Gong, et al. (1997) Gene Ther. 4, 1023-1028). Similarly, adenovirus-based systems may be used (see, for example, Wan et al. (1997) Hum. Gene Ther. 8, 1355-1363); retroviral systems may be used (Specht et al. (1997) J. Exp. Med. 186, 1213-1221 and Szabolcs et al. (1997). Blood particle-mediated transfer to dendritic cells may also be used (Tuting et al. (1997) Eur. J. Immunol. 27, 2702-2707); and RNA may also be used (Ashley et al. (1997)J. Exp. Med. 186, 1177 1182).

Generally, a pharmaceutical composition of the invention containing (a) nucleic acid(s) of the invention can be administered in a similar manner as those containing peptide(s) of the invention, e.g. intravenously, intra-arterially, intra-peritoneally, intramuscularly, intratumorally, orally, dermally, nasally, buccally, rectally, vaginally, by inhalation, or by topical administration.

Due to evasion mechanisms, a tumour often develops resistance to the treatment drug. The drug resistance may occur during treatment or manifest itself in metastases and recurring tumours. To avoid such a drug resistance, a tumour is commonly treated by a combination of drugs. Metastases and tumours recurring after a disease-free period of time often require a different combination. Therefore, in one aspect of the invention, the pharmaceutical composition is administered in conjunction with a second anticancer agent. The second anticancer agent may be administered before, after, or simultaneously with, the pharmaceutical composition of the invention. A simultaneous administration can e.g. be achieved by mixing the pharmaceutical composition of the invention with the second anticancer agent if their chemical properties are compatible. Another method of a simultaneous administration is the administration of the composition and anticancer agent on the same day independently from the route of administration. For example, the pharmaceutical composition of the invention may be injected while the second anticancer agent may be given orally. The pharmaceutical composition and second anticancer agent may also be administered within the same treatment course but on different days and/or within separate treatment courses.

In another aspect, the present invention provides a method for treating or preventing a cancer in a patient comprising administering to the patient a therapeutically effective amount any one of the pharmaceutical compositions of the invention.

A therapeutically effective amount will be an amount sufficient to induce an immune response, in particular an activation of a subpopulation of CTLs. A person skilled in the art may easily determine whether an amount is effective by using standard immunological methods, such as those provided in the examples of the present specifications. Another way of monitoring the effect of a certain amount of the pharmaceutical composition is to observe the growth of the tumour treated and/or its recurrence.

In a particularly preferred embodiment of the present invention, the pharmaceutical composition is used as an anticancer vaccine.

The composition containing peptides or peptide-encoding nucleic acids can also constitute a tumour or cancer vaccine. It may be administered directly into the patient, into the affected organ or systemically, or applied ex vivo to cells derived from the patient or a human cell line, which are subsequently administered to the patient, or used in vitro to select a subpopulation from immune cells derived from the patient, which are then re-administered to the patient.

The composition of the invention may be used in a method for treating of or used as a vaccine for cancer. The cancer may be of the buccal cavity and pharynx, cancer of the digestive tract, cancer of the colon, rectum, and anus, cancer of the respiratory tract, breast cancer, cancer of the cervix uteri, vagina, and vulva, cancer of the uterine corpus and ovary, cancer of the male genital tract, cancer of the urinary tract, cancer of the bone and soft tissue, and kaposi sarcoma, melanoma of the skin, eye melanoma, and non-melanoma eye cancer, cancer of the brain and central nervous system, cancer of the thyroid and other endocrine glands, Hodgkin Lymphoma, Non-Hodgkin Lymphoma, and myeloma, preferably renal cancer, colorectal cancer, lung cancer, breast cancer, pancreatic cancer, prostate cancer, gastric cancer, GIST or glioblastoma.

In the most preferred embodiment, methods of treatment utilize vaccines of the present invention comprising a multiple peptide tumour vaccine for treatment of colorectal carcinoma. Preferably, the vaccine comprises a set of tumour-associated peptides selected from SEQ ID NO: 1 to 15, which are located and have been identified on primary colorectal cancer cells. This set includes HLA class I and class II peptides. The peptide set may also contain at least one peptide, such as from HBV core antigen, used as a positive control peptide serving as immune marker to test the efficiency of the intradermal administration. In one particular embodiment, the vaccine consists of 14 individual peptides (according to SEQ ID NO: 1 to 15) or 13 individual peptides excluding the HBV core antigen with between about 1500 µg to about 75 µg, preferably between about 1000 µg to about 750 µg and more preferred between about 500 µg to about 600 µg, and most preferred about 578 µg of each peptide, all of which may be purified by HPLC and ion exchange chromatography and appear as a white to off-white powder. The lyophilisate is preferably dissolved in sodium hydrogen carbonate, and is used for intradermal injection within 30 min after reconstitution at room temperature. According to the present invention, preferred amounts of peptides can vary between about 0,1 and 100 mg, preferably between about 0,1 to 1 mg, and most preferred between about 300 µg to 800 µg per 500 µg of solution. Herein, the term "about" shall mean +/−10 percent of the given value, if not stated differently. The person of skill will be able to adjust the actual amount of peptide to be used based on several factors, such as, for example, the immune status of the individual patient and/or the amount of TUMAP that is presented in a particular type of cancer. The peptides of the present invention might be provided in other suitable forms (sterile solutions, etc.) instead of a lyophilisate.

The pharmaceutical preparation of the present invention comprising peptides, and/or nucleic acid(s) according to the invention is administered to a patient that suffers from an adenomateous or cancerous disease that is associated with the respective peptide or antigen. By this, a T cell-mediated immune response can be triggered.

It is preferred that a pharmaceutical composition according to the invention, wherein the amount of (in particular tumour associated) peptide(s), of nucleic acid(s), or expression vector(s) according to the invention is/are tissue, cancer, and/or patient-specific.

In another embodiment of the invention, the vaccine is a nucleic acid vaccine. It is known that inoculation with a nucleic acid vaccine, such as a DNA vaccine, encoding a polypeptide leads to a T-cell response. It may be administered directly into the patient, into the affected organ or systemically, or applied ex vivo to cells derived from the patient or a human cell line, which are subsequently administered to the patient, or used in vitro to select a subpopulation from immune cells derived from the patient, which are then re-administered to the patient. If the nucleic acid is administered to cells in vitro, it may be useful for the cells to be transfected so as to co-express immune-stimulating cytokines, such as interleukin-2 or GM-CSF. The nucleic acid(s) may be substantially pure, or combined with an immune-stimulating adjuvant, or used in combination with immune-stimulatory cytokines, or be administered with a suitable delivery system, for example liposomes. The nucleic acid vaccine may also be administered with an adjuvant such as those described for peptide vaccines above. Preferably the nucleic acid vaccine is administered without adjuvant.

The polynucleotide may be substantially pure, or contained in a suitable vector or delivery system. Suitable vectors and delivery systems include viral, such as systems based on adenovirus, vaccinia virus, retroviruses, herpes virus, adeno-associated virus or hybrids containing elements of more than one virus. Non-viral delivery systems include cationic lipids and cationic polymers as are well known in the art of DNA delivery. Physical delivery, such as via a "gene-gun," may also be used. The peptide or peptide encoded by the nucleic acid may be a fusion protein, for example with an epitope from tetanus toxoid that stimulates CD4-positive T-cells.

Suitably, any nucleic acid administered to the patient is sterile and pyrogen free. Naked DNA may be given intramuscularly or intradermally or subcutaneously. Conveniently, the nucleic acid vaccine may comprise any suitable nucleic acid delivery means. The nucleic acid, preferably DNA, may also be delivered in a liposome or as part of a viral vector delivery system. It is preferred if the nucleic acid vaccine, such as DNA vaccine, is administered into the muscle, whilst peptide vaccines are preferably administered s.c. or i.d. It is also preferred that the vaccine is administered into the skin.

It is believed that uptake of the nucleic acid and expression of the encoded polypeptide by professional antigen presenting cells, such as dendritic cells, may be the mechanism of priming of the immune response; however, dendritic cells may not be transfected but are still important since they may pick up expressed peptide from transfected cells in the tissue ("cross-priming," e.g., Thomas A M, et al., J Exp Med. 2004 August 2;200(3):297-306).

Polynucleotide-mediated immunization therapy of cancer is described in Conry et al. (1996) Seminars in Oncology 23,135-147; Condon et al. (1996) Nature Medicine 2,1122-1127; Gong et al. (1997) Nature Medicine 3,558-561; Zhai et al. (1996) J. Immunol. 156,700-710; Graham et al. (1996) Int J. Cancer 65,664-670; and Burchell et al. (1996) pp 309-313 In: Breast Cancer, Advances in biology and therapeutics, Calvo et al. (eds), John Libbey Eurotext, all of which are incorporated herein by reference in their entireties.

It may also be useful to target the vaccine to specific cell populations, for example antigen presenting cells, either by the site of injection, use of targeting vectors and delivery systems, or selective purification of such a cell population from the patient and ex vivo administration of the peptide or nucleic acid (for example dendritic cells may be sorted as described in Zhou et al. (1995) Blood 86, 3295-3301; Roth et al. (1996) Scand. J. Immunology 43,646-651). For example, targeting vectors may comprise a tissue-or tumour-specific promoter that directs expression of the antigen at a suitable place.

Finally, vaccines according to the invention can be dependent from the specific type of cancer, as well as the status of the disease, earlier treatment regimens, the immune status of the patient, and, of course, the HLA-haplotype of the patient. Furthermore, the vaccine according to the invention can contain individualized components, according to personal needs of the particular patient. Examples include different amounts of peptides according to the expression of the related TAAs in the particular patient, unwanted side-effects due to personal allergies or other treatments, and adjustments for secondary treatments following a first round or scheme of treatment.

In addition to being useful for treating cancer, the peptides of the present invention are also useful as diagnostics. Since the peptides were generated from glioblastoma and since it was determined that these peptides are not present in normal tissues, these peptides can be used to diagnose the presence of a cancer.

The presence of the peptides of the present invention on tissue biopsies can assist a pathologist in diagnosis of cancer. Detection of certain peptides of the present invention by means of antibodies, mass spectrometry or other methods known in the art can tell the pathologist that the tissue is malignant or inflamed or generally diseased. Presence of groups of peptides of the present invention can enable classification or subclassification of diseased tissues.

The detection of the peptides of the present invention on diseased tissue specimen can enable the decision about the benefit of therapies involving the immune system, especially if T lymphocytes are known or expected to be involved in the mechanism of action. Loss of MHC expression is a well described mechanism by which infected of malignant cells escape immunosurveillance. Thus, presence of the peptides of the present invention shows that this mechanism is not exploited by the analyzed cells.

The peptides of the present invention might be used to analyze lymphocyte responses against those peptides of the present invention, such as T cell responses or antibody responses against the peptides of the present invention or the peptides of the present invention complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against the peptides of the present invention can be considered in the assessment of side effects. Monitoring of lymphocyte responses might also be a valuable tool for follow-up examinations of transplantation therapies, e.g. for the detection of graft versus host and host versus graft diseases.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes, such as PET. This use can help to detect small metastases or to determine the size and precise localization of diseased tissues. In addition, the peptides can be used to verify a pathologist's diagnosis of a cancer based on a biopsied sample.

In yet another aspect thereof, the present invention relates to a kit comprising (a) a container that contains a pharmaceutical composition as described above, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contains instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 g). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, a anti-angiogenesis agent or inhibitor, a apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The pharmaceutical formulation of the present invention is one that is suitable for administration of the peptides by any acceptable route such as oral (enteral), nasal, ophthal, subcutaneous, intradermal, intramuscular, intravenous or transdermal. Preferably the administration is s.c., and most preferably, i.d. Administration may be by infusion pump.

It should be understood that the features of the invention as disclosed and described herein can be used not only in the respective combination as indicated but also in a singular fashion without departing from the intended scope of the present invention. For the purposes of the present invention, all references as cited herein are incorporated by reference in their entireties.

The following examples are provided for illustrative purposes only and are not intended to limit the invention.

EXAMPLES

Example 1

Components of the Exemplary Pharmaceutical Composition IMA910-A

IMA910-A is composed of a cocktail of synthetic tumor associated peptides (TUMAPs) of which the majority has been identified on primary colorectal cancer cells. The TUMAPs include 10 HLA class I-binding peptides with the capacity to activate cytotoxic T cells (CD 8+ T cells) and 3 HLA class II-binding peptides with the capacity to activate T helper cells (CD4+ T cells). T helper cells play a crucial role in assisting the function of cytotoxic T cells by releasing cytokines which enhance the killer function of CD8+ T cells and may also act directly against tumor cells (Knutson, K L and Disis, M L; 2005, Curr. Drug Targets. Immune. Endocr. Metabol. Disord., 5, 365-371). In addition to these 13 TUMAPs, IMA910-A contains one viral control peptide.

Samples from surgically removed malignant and normal tissue from CRC patients and blood from healthy donors were analyzed in a stepwise approach: First genome-wide mRNA expression analysis by microarrays was used to identify genes overexpressed in the malignant tissue compared with a range of normal organs and tissues. In a second step, HLA ligands from the malignant material were identified by mass spectrometry.

Subsequently identified HLA ligands were compared to gene expression data. Peptides encoded by selectively expressed or overexpressed genes as detected in step 1 were considered suitable candidate TUMAPs for a multi-peptide vaccine. A literature search was performed to identify additional evidence supporting the relevance of the identified peptides as TUMAPs. Finally, peripheral CD8+ T cells of healthy individuals were tested for reactivity against the tumor-associated HLA ligands using several immunoassays (in vitro T-cell assays).

TABLE 3

IMA910-A TUMAP composition.

| TUMAP ID | Name | Function/Comments |
|---|---|---|
| HLA-A*02 TUMAPs | | |
| C20-001 | Chromosome 20 open reading frame 42 | Poorly characterized, strong overexpression |
| CCN-001 | Cyclin D1 | Cell cycle regulation, frequently upregulated in many cancer types |
| CEA-004 | Carcinoembryonic antigen-related cell adhesion molecule 5 (CEA) | Well-established TAA in CRC, cell adhesion, metastasis |
| MET-001 | Met proto-oncogene | Proliferation, motility, adhesion, invasion |
| MUC-001 | Mucin 1 | Well-established TAA in CRC, unmasking of epitope due to altered glycosylation in tumors |
| NOX-001 | NADPH oxidase 1 | Strong overexpression, inhibition of apoptosis |
| ODC-001 | Ornithine decarboxylase 1 | Transformation, pro-angiogenic |
| PCN-001 | Proliferating cell nuclear antigen | Proliferation (DNA replication) |
| TGFBI-001 | Transforming growth factor beta-induced | Tissue remodelling, angiogenesis |
| TOP-001 | Topoisomerase (DNA) II | Proliferation (DNA replication) |
| HLA-DR TUMAPs | | |
| CEA-006 | Carcinoembryonic antigen-related cell adhesion molecule 5 (CEA) | Well-established TAA in CRC, cell adhesion, metastasis |
| MMP-001 | Matrix metallopeptidase 7 (matrilysin, uterine) | Tissue remodelling, inhibition of apoptosis |
| TGFBI-004 | Transforming growth factor beta-induced | Tissue remodelling, angiogenesis |

IMA910-A contains 10 HLA-A*02 (class I) and 3 HLA-DR (class II) TUMAPs. In addition, the viral marker peptide HBV-001 will be included, which is not listed here.

Example 2

Presentation of Epitopes Contained in IMA910-A in Tumour Samples

Preparation

Surgically removed tissue specimens were provided by Universitätsklinik für Allgemeine, Viszeral- und Transplantationschirurgie, Tübingen after written informed consent had been obtained from each patient.

Isolation of HLA Peptides from Tissue Samples

HLA peptide pools from shock-frozen tissue samples were obtained by immune precipitation from solid tissues according to a slightly modified protocol (Falk, K., et al., Nature 351, 290-296 (1991); Seeger, F. H. et al. Immunogenetics 49, 571-576 (1999)) using the HLA-A*02-specific antibody BB7.2 or the HLA-A, -B, -C-specific antibody W6/32, CNBr-activated sepharose, acid treatment and ultrafiltration.

Detection of TUMAPs by ESI-liquid Chromatography Mass Spectrometry (ESI-LCMS)

Colorectal tumor samples were searched systematically by mass spectrometry for epitopes contained in IMA910-A. The obtained HLA peptide pools were separated according to their hydrophobicity by reversed-phase chromatography (CapLC, Waters) and the eluting peptides were analyzed in a hybrid quadrupole orthogonal acceleration time of flight tandem mass spectrometer (Q-TOF Ultima, Waters) equipped with an ESI source. Peptide pools were loaded onto a C18 pre-column for concentration and desalting. After loading, the pre-column was placed in line for separation by a fused-silica micro-capillary column (75 μm i.d. ×250 mm) packed with 5 μm C18 reversed-phase material (Dionex). Solvent A was 4 mM ammonium acetate/water. Solvent B was 2 mM ammonium acetate in 80% acetonitrile/water. Both solvents were adjusted to pH 3.0 with formic acid. A binary gradient of 15% to 60% B within 90 minutes was performed, applying a flow rate of 5 μl/min reduced to approximately 200 nl/min by a split-system. A gold coated glass capillary (PicoTip, New Objective) was used for introduction into the micro-ESI source. The integration time for the TOF analyzer was 1.9 s with an interscan delay of 0.1 s. For detection of defined peptides, high sensitive screening was performed in this type of ESI-LCMS experiment on the basis of known molecular weights and retention times of the peptides in the chromatographic system. Therefore, a list containing the m/z values of the previously identified peptides (singly and/or doubly charged) was applied to precursor selection. Subsequently, the sequence was revealed by collisionally induced decay (CID) mass spectrometry (ESI-LCMS/MS). The TUMAP sequence was assured by comparison of the generated natural TUMAP fragmentation pattern with the fragmentation pattern of a synthetic sequence-identical reference peptide. Evaluation of the HLA peptide purification yield and reproducibility of the analytical system, including retention time stability was carried out using the intensity and retention time of an abundant endogenous HLA-A*02 peptide (YLLPAIVHI from DDX5) as internal standard. Therefore, the CRC sample inclusion criterion for detection of previously identified TUMAP in these experiments was set to a minimal intensity of 650 counts per scan of the internal doubly charged standard signal (YLLPAIVHI) in the LCMS/MS experiment to assure a successful HLA peptide isolation and the correct performance of the analytical system.

Table 4 shows the results of an analysis of colon and rectum cancer samples of different stages as well as metastases originating from either primary tumour site. All HLA-A*02 TUMAPs were found on the majority of samples. Re-detection frequencies of HLA-DR TUMAPs are generally lower. This can be expected because HLA class II peptides have several length variants for each core sequence.

TABLE 4

Re-detection of TUMAPS in CRC samples

| | | | | TUMAP detected (+) or not detected (−) in mass spectrometric analysis | | | | | | |
|---|---|---|---|---|---|---|---|---|---|---|
| | Tumor | | | Class I | | | | | | |
| CRC No | CRC sample | mass [g] | Tumor location | Tumor stage | MET-001 | C20-001 | TGFBI-001 | TOP-001 | NOX-001 | PCN-001 | ODC-001 |
| 1 | CCA062 | ? | colon | I | n.a | n.a | n.a | n.a | n.a | n.a | n.a |
| 2 | CCA740 | 4.0 | colon | II | − | + | + | + | + | + | + |
| 3 | CCA165 | 10.8 | colon | II | − | + | + | + | + | + | + |
| 4 | CCA712 | 1.2 | Colon | III | + | + | + | + | − | − | + |
| 5 | CCA707 | 3.1 | colon | III | − | + | + | + | + | + | + |
| 6 | CCA718 | 3.4 | colon | III | − | + | + | + | + | + | + |
| 7 | CCA739 | 3.4 | colon | III | − | + | + | + | + | + | + |
| 8 | CCA166 | 5.3 | colon | III | + | + | + | + | + | + | + |
| 9 | CCA734 | 18.1 | colon | III | − | + | + | + | + | + | + |
| 10 | CCA719 | 1.3 | colon | IV | − | + | + | + | + | − | + |
| 11 | CCA725 | 2.7 | colon | IV | − | + | + | + | − | + | + |
| 12 | CCA164 | 5.0 | colon | IV | + | + | + | − | − | + | + |
| 13 | CCA167 | 5.2 | colon | IV | n.a. | n.a. | n.a. | n.a. | n.a. | n.a. | n.a. |
| 14 | CCA056 | 1.8 | colon | ? | n.a. | n.a. | n.a. | n.a. | n.a. | n.a. | n.a. |
| 15 | CCA305 | 4.0 | colon | ? | n.a. | n.a. | n.a. | n.a. | n.a. | n.a. | n.a. |
| 20 | CCA708 | 3.2 | colon metastasis | IV | − | + | + | + | + | + | + |
| 16 | CCA160 | 3.6 | rectum | II | + | + | + | + | + | + | + |
| 17 | CCA754 | 3.6 | rectum | II | − | + | + | + | − | + | + |

TABLE 4-continued

Re-detection of TUMAPS in CRC samples

| | CRC sample | Tumor mass [g] | Tumor location | Tumor stage | | | | | | | |
|---|---|---|---|---|---|---|---|---|---|---|---|
| 18 | CCA170 | 4.6 | rectum | III | n.a. | n.a. | n.a. | n.a. | n.a. | n.a. | n.a. |
| 19 | CCA171 | 10.3 | rectum | IV | n.a. | n.a. | n.a. | n.a. | n.a. | n.a. | n.a. |
| 21 | CCA724 | 4.8 | rectum metastasis | IV | + | + | + | – | – | – | + |
| | Detected in % of analyzed samples | | | | 33% | 100% | 100% | 87% | 67% | 80% | 100% |

| | | | | | TUMAP detected (+) or not detected (–) in mass spectrometric analysis | | | | | |
|---|---|---|---|---|---|---|---|---|---|---|
| | | Tumor | | | Class I | | | Class II | | |
| | CRC No sample | mass [g] | Tumor location | Tumor stage | CCN-001 | MUC-001 | CEA-004 | CEA-006 | MMP-001 | TGFBI-004 |
| 1 | CCA062 | ? | colon | I | not feasible | not feasible | not feasible | – | – | – |
| 2 | CCA740 | 4.0 | colon | II | | | | n.a | n.a | n.a |
| 3 | CCA165 | 10.8 | colon | II | | | | – | – | – |
| 4 | CCA712 | 1.2 | Colon | III | | | | n.a | n.a | n.a |
| 5 | CCA707 | 3.1 | colon | III | | | | n.a | n.a | n.a |
| 6 | CCA718 | 3.4 | colon | III | | | | n.a | n.a | n.a |
| 7 | CCA739 | 3.4 | colon | III | | | | n.a | n.a | n.a |
| 8 | CCA166 | 5.3 | colon | III | | | | (+) | + | – |
| 9 | CCA734 | 18.1 | colon | III | | | | n.a | n.a | n.a |
| 10 | CCA719 | 1.3 | colon | IV | | | | n.a | n.a | n.a |
| 11 | CCA725 | 2.7 | colon | IV | | | | n.a | n.a | n.a |
| 12 | CCA164 | 5.0 | colon | IV | | | | – | – | – |
| 13 | CCA167 | 5.2 | colon | IV | | | | (+) | + | – |
| 14 | CCA056 | 1.8 | colon | ? | | | | – | – | – |
| 15 | CCA305 | 4.0 | colon colon | ? | | | | – | – | – |
| 20 | CCA708 | 3.2 | colon metastasis | IV | | | | – | + | + |
| 16 | CCA160 | 3.6 | rectum | II | | | | + | (+) | + |
| 17 | CCA754 | 3.6 | rectum | II | | | | n.a. | n.a. | n.a. |
| 18 | CCA170 | 4.6 | rectum | III | | | | (+) | – | + |
| 19 | CCA171 | 10.3 | rectum | IV | | | | – | + | – |
| 21 | CCA724 | 4.8 | rectum metastasis | IV | | | | – | – | + |
| | Detected in % of analyzed samples | | | | – | – | – | 33% | 42% | 33% | n.a. not analyzed

Example 3

In vitro Immunogenicity for IMA910-A MHC Class I Presented Peptides

To obtain information regarding the immunogenicity of peptides included in IMA910-A, investigations using a well established in vitro stimulation platform already described by (Walter, S, et al., 2003, J. Immunol., 171, 4974-4978) were performed. Positive immunogenicity data for 10/10 tested HLA-A*0201 restricted peptides contained in IMA910-A demonstrating that these peptides are T-cell eptiopes against which CD8+ precursor T cells exist in humans could be shown. The only other HLA class I peptide contained in IMA910-A (MUC-001) could not be tested with this method due to the relative low A*0201 affinity of this TUMAP.

CEA-004

Recent evidence severely challenges the usefulness of CEA-005 for a cancer vaccine. In a recent comprehensive study (Iero, M, et al., 2007, Cancer Immunol. Immunother., electronic publication ahead of print) the authors for the first time systematically characterized effector functions of CEA-005-primed T cells against the native sequence CEA-004. For a large number of blood samples from CRC patients and healthy donors, it was observed that T-cell priming with CEA-005 reproducibly promoted the generation of low-affinity T cells lacking the ability to recognize CEA-expressing colorectal carcinoma cells presenting the native sequence. Such non-effective low-affinity cross-recognition of native sequences might be a general problem in vaccination protocols using altered peptide ligands, as corroborated by recently reported similar results for another CEA peptide and its altered agonists (Alves, P M, et al., 2007, Cancer Immunol. Immunother., 56, 1795-1805). Furthermore, such results have also been reported for a native sequence of the well-established melanoma antigen Melan-A/MART-1 and its agonist (D. Speiser, personal communication).

Altogether, despite the generally enhanced immunogenicity of altered agonist peptides, recent evidence suggests that native peptides might be more attractive vaccine candidates due to inefficient cross-recognition of the native sequence by T cells stimulated with altered agonists. This suggests that CEA-004 (CAP 1) should be preferred to its agonists described in WO9919478A1, like CEA-005 (CAP1-6D) or CAP 1-6D,7I.

In fact, ample data demonstrate considerable in vivo immunogenicity of the native CEA-004 sequence itself. Spontaneously induced T cell responses against this peptide among cancer patients but not healthy donors have been observed in several studies (Nagorsen, D, et al., 2000, Cancer Res. 60, 4850-4854; Weihrauch, M R, et al., 2005, Clin Cancer Res. 11, 5993-6001; Babatz, J, et al., 2006, Cancer Immunol. Immunother. 55, 268-276). Furthermore, vaccination approaches in CRC patients using CEA-004 or CEA protein have demonstrated efficient stimulation of T-cell responses against CEA-004 (Tsang, K Y, et al., 1995, J Natl. Cancer Inst.

87, 982-990; Morse, M A, et al., 1999, Clin Cancer Res. 5, 1331-1338; Zhu, M Z, et al., 2000, Clin Cancer Res. 6, 24-33; Weihrauch, M R, et al., 2005, Clin Cancer Res. 11, 5993-6001).

In vitro Priming of CD8+ T Cells

To perform in vitro stimulations by artificial antigen presenting cells (aAPC) loaded with peptide-MHC complex (pMHC) and anti-CD28 antibody, PBMCs (peripheral blood mononuclear cells) from fresh HLA-A*02+ buffy coats were isolated by using standard density gradient separation medium (PAA, Cölbe, Germany). Buffy coats were either obtained from the Blood Bank Tübingen or from the Katharinenhospital Stuttgart. Isolated PBMCs were incubated overnight in T-cell medium (TCM) for human in vitro priming consisting of RPMI-Glutamax (Invitrogen, Karlsruhe, Germany) supplemented with 10% heat inactivated human AB serum (PAA, Cölbe, Germany), 100 U/ml Penicillin/100 µg/ml Streptomycin (Cambrex, Verviers, Belgium), 1 mM sodium pyruvate (CC Pro, Neustadt, Germany) and 20 µg/ml Gentamycin (Cambrex). CD8+ lymphocytes were isolated using the CD8+ MACS positive selection kit (Miltenyi, Bergisch Gladbach, Germany) according to the manufacturer's instructions. Obtained CD8+ T-cells were incubated until use in TCM supplemented with 2.5 ng/ml IL-7 (PromoCell, Heidelberg, Germany) and 10 U/ml IL-2 (Chiron, Munich, Germany). Generation of pMHC/anti-CD28 coated beads, T-cell stimulations and readout was performed as described before (Walter, S, et al., 2003, J. Immunol., 171, 4974-4978) with minor modifications. Briefly, biotinylated recombinant HLA-A*0201 molecules lacking the transmembrane domain and biotinylated at the carboxy terminus of the heavy chain were produced following a method described by (Altman, J D, et al., 1996, Science, 274, 94-96). The purified costimulatory mouse IgG2a anti human CD28 Ab 9.3 (Jung, G, et al., 1987, Proc Natl Acad Sci USA, 84, 4611-4615) was chemically biotinylated using Sulfo-N-hydroxysuccinimidobiotin as recommended by the manufacturer (Perbio, Bonn, Germany). 5.60 µm large streptavidin coated polystyrene particle beads were used (Bangs Laboratories, Illinois/USA). pMHC used as positive and negative controls were A*0201/MLA-001 (peptide ELAGIGILTV from modified Melan-A/MART-1) and A*0201/DDX5-001 (YLLPAIVHI from DDX5) or A*0201/HBV-001 (FLPSDFFPSV), respectively.

800,000 beads/200 µl were coated in 96-well plates in the presence of 600 ng biotin anti-CD28 plus 200 ng relevant biotin-pMHC (high density beads) or 2 ng relevant plus 200 ng irrelevant (pMHC library) MHC (low density beads). Stimulations were initiated in 96-well plates by conincubating 1×10⁶ CD8+ T cells with 2×10⁵ washed coated beads in 200 µl TCM supplemented with 5 ng/ml IL-12 (PromoCell) for 3-4 days at 37° C. Half of the medium was then exchanged by fresh TCM supplemented with 80 U/ml IL-2 and incubating was continued for 3-4 days at 37° C. This stimulation cycle was performed for a total of three times. Finally, tetrameric analyses were performed with fluorescent MHC tetramers (produced as described by (Altman, J D, et al., 1996, Science, 274, 94-96)) plus antibody CD8-FITC clone SK1 (B D, Heidelberg, Germany) on a four-color FACSCalibur (BD). Peptide specific cells were calculated as percentage of total CD8+ T cells. Evaluation of tetrameric analysis was done using the software FCS Express (De Novo Software). In vitro priming of specific tetramer+ CD8+ lymphocytes was detected by appropriate gating and by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific tetramer+ among CD8+ T-cells and the percentage of specific tetramer+ cells was at least 10× the median of the negative control stimulations).

In vitro Immunogenicity for 10 Peptides in the IMA910-A Vaccine

For 10/10 tested HLA class I peptides, in vitro immunogenicity could be demonstrated by generation of peptide specific T-cell lines. A representative staining showing generation of T-cell lines specifc for NOX-001 and ODC-001 is shown in FIG. 1. The results are summarized in table 5. The only other HLA class I peptide contained in IMA910-A (MUC-001) could not be tested with this method due to relative low A*0201 affinity of this TUMAP, therefore rendering it methodologically impossible to perform in vitro stimulations using pMHC monomers.

TABLE 5

Immunogenicity of 10 HLA class I peptides included in IMA910-A

| Antigen | Positive donors/donors tested | Positive wells/wells tested |
|---|---|---|
| IMA-HBV-001 | 7/16 (44%) | 10/107 (9%) |
| IMA-TGFBI-001 | 3/4 (75%) | 4/22 (18%) |
| IMA-NOX-001 | 3/5 (60%) | 9/60 (15%) |
| IMA-PCN-001 | 3/4 (75%) | 4/42 (10%) |
| IMA-TOP-001 | 2/5 (40%) | 7/72 (10%) |
| IMA-C20-001 | 1/5 (20%) | 1/60 (2%) |
| IMA-ODC-001 | 1/5 (20%) | 1/60 (2%) |
| IMA-HBV-001 | 2/5 (40%) | 10/54 (19%) |
| IMA-CEA-004 | 4/4 (100%) | 50/60 (83%) |
| IMA-CCN-001 | 5/5 (100%) | 42/54 (78%) |
| IMA-MET-001 | 4/6 (67%) | 30/72 (42%) |

Results of in vitro immunogenicity experiments for 10 of 11 HLA class I peptides included in IMA910-A are summarized here. Results were obtained by stimulation of CD8+ cells with high density beads. As different human serum lots may highly affect the immunogenicity results, only assays in which one and the same serum lot was used, were evaluated together.

IMA-CEA-004 in vitro Primed T-cells

4/6 donors were evaluable. In all four donors we were able to show successfully the induction of CEA-004-directed T cell response in vitro upon stimulation with CEA-004 (see Table A and FIG. 5). Thus, CEA-004 peptide proved to be a potent inducer of human CD8+ T-cell responses in vitro. Importantly, CEA-004 was reproducibly capable of eliciting higher frequencies of CEA-004 specific T cell responses as compared to CEA-005 (83% of wells as compared to 64% of wells, see Table B). Frequencies of CEA-004 specific cells within individual positive wells were also higher after CEA-004 priming as compared to CEA-005 priming (see FIG. 6).

Peptide-specific in vitro CD8+ T-cell Response of 4 Healthy HLA-A*02 Donors Determined by Flow Cytometric Analysis CD8+ T cells were primed using artificial antigen presenting cells loaded with CEA-004, CEA-005 or irrelevant peptide (IMA-RSL-001), respectively. After three cycles of stimulation, the detection of peptide-reactive cells was performed by double staining with CEA-004-plus CEA-005 tetramers (Resulsts shown in A below) and with CEA-004-plus irrelevant A*0201-tetramer (results shown in B below). The numbers indicated in the table represent percentages of wells containing either CEA-004+ or CEA-005+ CTLs. The lot of human serum used for all experiments was C02104-0167.

| Antigenic stimulus | Wells with CEA-004+ tetramer+ Cells |
|---|---|
| A. | |
| CEA-004 | 50/60 (83%) |
| CEA-005 | 19/72 (26%) |
| B. | |
| CEA-004 | 50/60 (83%) |
| CEA-005 | 46/72 (64%) |

Figure 5:
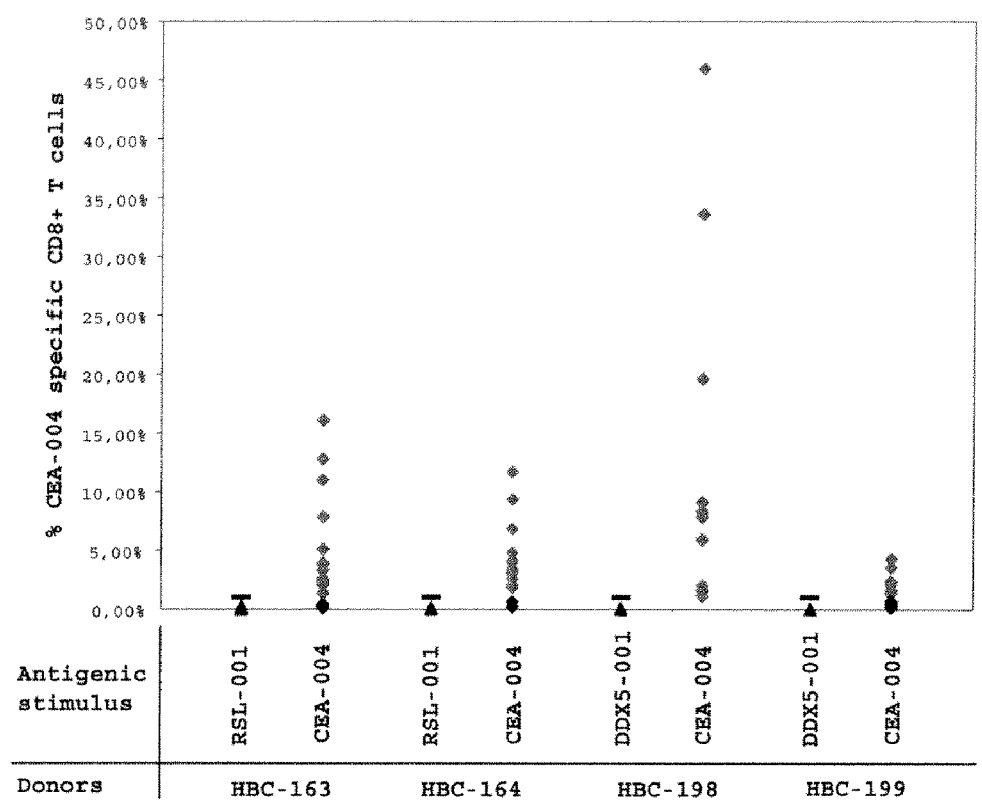
FIG. 5: Frequencies of CEA-004-specific CD8+ T cells in 4 HLA-A2 healthy donors following in vitro stimulation with CEA-004 as determined by flow cytometric analysis.
Figure 6:
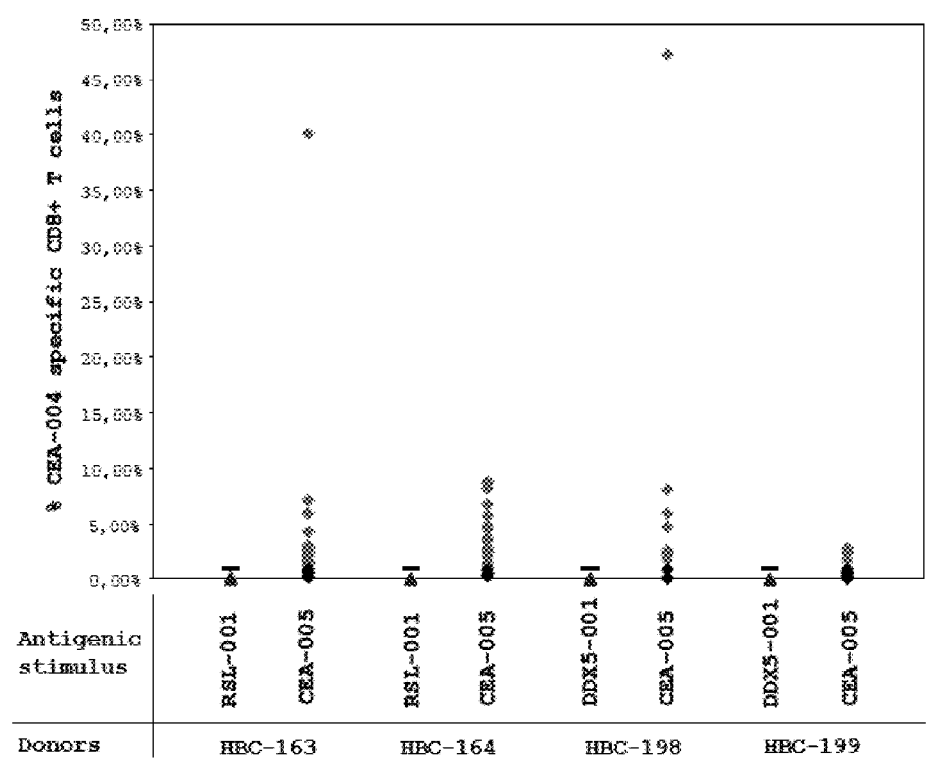
FIG. 6: Frequencies of CEA-004-specific CD8+T cells in 4 HLA-A2 healthy donors following in vitro stimulation with CEA-005 as determined by flow cytometric analysis.

FIG. 5 shows the frequencies of CEA-004-specific CD8+ T cells in 4 HLA-A2 healthy donors following in vitro stimulation with CEA-004 as determined by flow cytometric analysis CD8+ T cells were isolated from PBMCs, primed in vitro using artificial antigen presenting cells loaded with CEA-004, RSL-001 or DDX5-001 peptide, respectively. After three cycles of stimulation, the detection of peptide-reactive cells was performed by staining with CEA-004- plus irrelevant A*0201-tetramers. The values indicated above represent the percentages of CEA-004 specific cells of each stimulated well. RSL-001 and DDX5-001 stimulations served as negative controls. Threshold values for positive wells are indicated for each donor separately (−) and were defined as 10 fold the median of the negative controls and at least 1%. Wells with percentage values above threshold ($\leq$1%) were considered positive and are represented by the pink rhombs, while negative wells are shown by black rhombs.

Example 4

In vitro Immunogenicity for IMA910-A MHC Class II Presented Peptides

T helper cells play an important role in supporting CTLs to activate and sustain immune responses against tumor cells. Therefore, MHC class II peptides were included in IMA910-A. TGFBI-004, one of the three class II peptides contained in IMA910-A, was tested for its immunogenic potential in vitro and proved to be an inducer of both specific CD4+ and CD8+ T cells. The generation of CD4+ and functional CD8+ T lymphocytes was shown in experiments using stimulations performed in an autologous system.

Principle of Test

Priming and expansion of specific human CD4+ and CD8+ cells were assayed in vitro by priming of monocyte-depleted PBMCs with autologous DCs and restimulation with autologous PBMCs. Briefly, to generate antigen-specific CD4+ T cells, monocyte-depleted PBMCs of one healthy donor (HLA genotype classI: A1/A25/B8/B18 and class II: DQB1*02/DQB1*06/DRB1*03/DRB1*15/DRB3/DRB5) were stimulated using peptide-pulsed autologous DCs and restimulated with autologous PBMCs plus peptide. As a read-out system, IFN$\gamma$ production upon short term restimulation was assessed by ELISPOT and flow cytometry. T cells were analyzed after eight stimulations by ELISPOT and intracellular IFN$\gamma$ staining plus CD4-FITC and CD8-PerCP to determine the percentage of IFN$\gamma$-producing cells in specific T-cell subpopulations. In this experiment, cells stimulated with TGFBI-004 peptide from different wells were pooled, incubated with irrelevant peptide for the read-out and performed as negative controls.

Generation of Dendritic Cells (DCs)

Human DCs were obtained from monocytes cultered in DC medium consisting of RPMI 1640-Glutamax/25mM Hepes (Invitrogen, Germany) supplemented with 10% autologous plasma, 100 U/ml penicillin and 100 µg/ml streptomycin. First, buffy coat and plasma was obtained by centrifugation of the blood from a healthy donor (Bloodbank Tübingen). PBMCs were then isolated from the buffy coat by standard density gradient separation (Lymphocyte Separation Medium, PAA, Austria) and resuspended in DC medium to determine total cell number. 100-120 Mio of PBMCs were washed, resuspended in 15 ml X-Vivo 20 medium (Bio Whittaker, Belgium) and transferred to a cell culture flask. After 2 hours at 37° C., media containing peripheral blood leukocytes (PBL) was removed, adherent monocytes were washed twice with 10 ml PBS and cultured for 6 days in 10 ml DC medium with 100 ng/ml GM-CSF and 30 ng/ml IL-4 (ImmunoTools, Germany) or 20 ng/ml (R&D systems, Germany). On day 3 and 5 100 ng/ml GM-CSF and 30 ng/ml IL-4 (Immunotools) or 20 ng/ml IL-4 (R&D Systems, Germany) was added. On day 7 immature DCs were activated with 10 ng/ml TNF-$\alpha$ (R&D Systems, Germany) and 20 µg/ml poly(IC) (Sigma Aldrich, Germany) or 100 ng/ml LPS for 24 hours. Remaining PBMCs and obtained PBLs were aliquoted and frozen.

In vitro Priming of Specific T Cells

To generate CD4+ T cells, 3 Million PBMCs/PBLs were stimulated with $2 \times 10^5$ autologuous DCs. DCs were harvested on day 8. PBS with 5 mM EDTA was used for this purpose to gain as many cells as possible (including adherent cells). After being washed with DC medium, cell number was determined. For loading with peptide, DCs were resuspended in 1 ml DC medium and incubated with 25 µg/ml peptide for 2 hours at 37° C. Peptides used for pulsing of DCs were TGFBI-004, Posmix (mix of EBV and CMV related peptides), Padre and CMV. Autologous PBMCs/PBLs were thawed, washed with DC medium (at least twice) and plated in a 24 well plate at a density of 3 Mio cells/ml in 1 ml. DCs loaded with peptide were then added (as 1 ml suspension containing the peptide) to the plated PBMCs/PBLs and incubated for 7 days at 37° C. After priminig, obtained CTLs were first restimulated with cryopreserved autologous peptide-loaded PBMCs which have been irradiated (30 Gy; Gammacell 1000 Elite, Nordion International, Canada). $5 \times 10^5$ CTLs and $2.5 \times 10^6$ PBMCs were added per well for this purpose. Pulsing of PBMCs with peptide was performed as aforementioned (for DCs). On day 1 after the first restimulation, IL-2 (R&D Systems, Germany) and IL-7 was added to a final concentration of 2 ng/ml and 5 ng/ml, respectively. Afterwards, every 2nd day and every 7th day IL-2 and IL-7 were added to the media. Second restimulation was done 7 days later, but this time peptide was added alone (without PBMCs) to the cultured CTLs. Restimulations were performed in a 7 day cycle, with peptide-loaded PBMCs and petide alone being added alternatively. Analyses were performed after the eight stimulation by intracellular IFN$\gamma$ staining and IFN$\gamma$ ELISPOT.

Results

Figure 2:
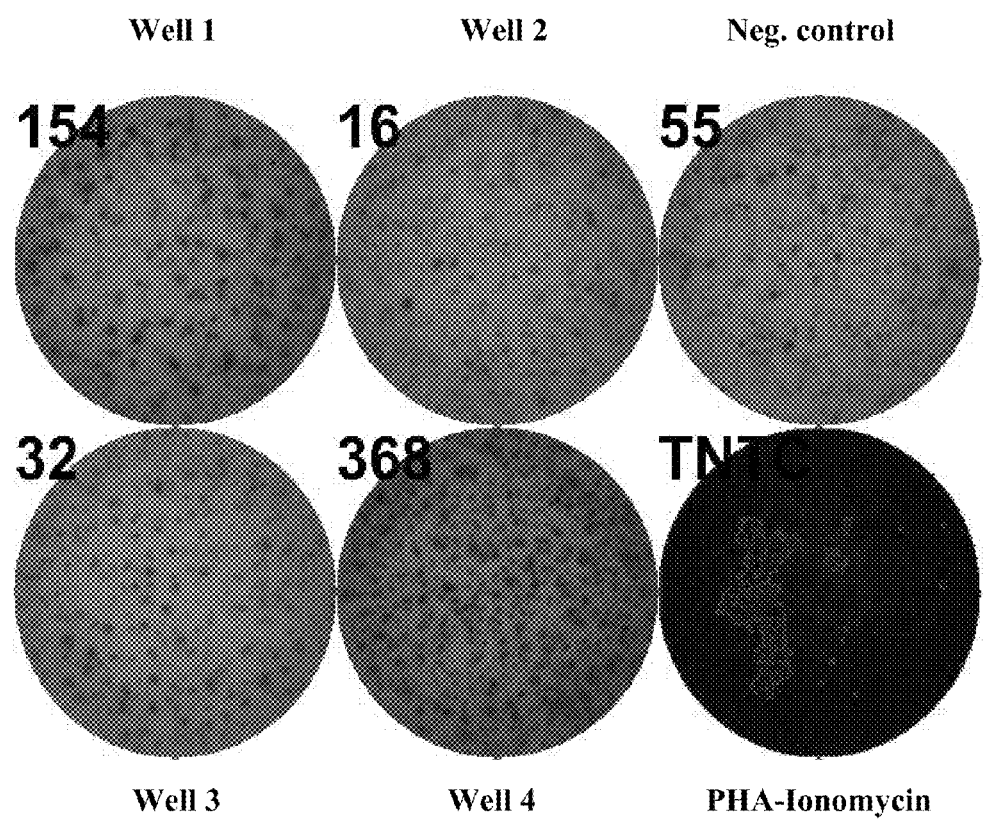
FIG. 2: In vitro immunogenicity of TGFBI-004 as detected by IFNγ ELISPOT after five stimulation cycles. Cells were primed and restimulated repeatedly with TGFBI-004 and then incubated with relevant TGFBI-004 (Well 1, 2, 3 and 4) and irrelevant (Neg. control) peptide, respectively. The analysis after IFNγ ELISPOT was performed on an ELISPOT Reader (CTL, Cleveland, USA). PHA-Ionomycin served as positive control. Numbers indicate the count of positive spots.
Figure 3:
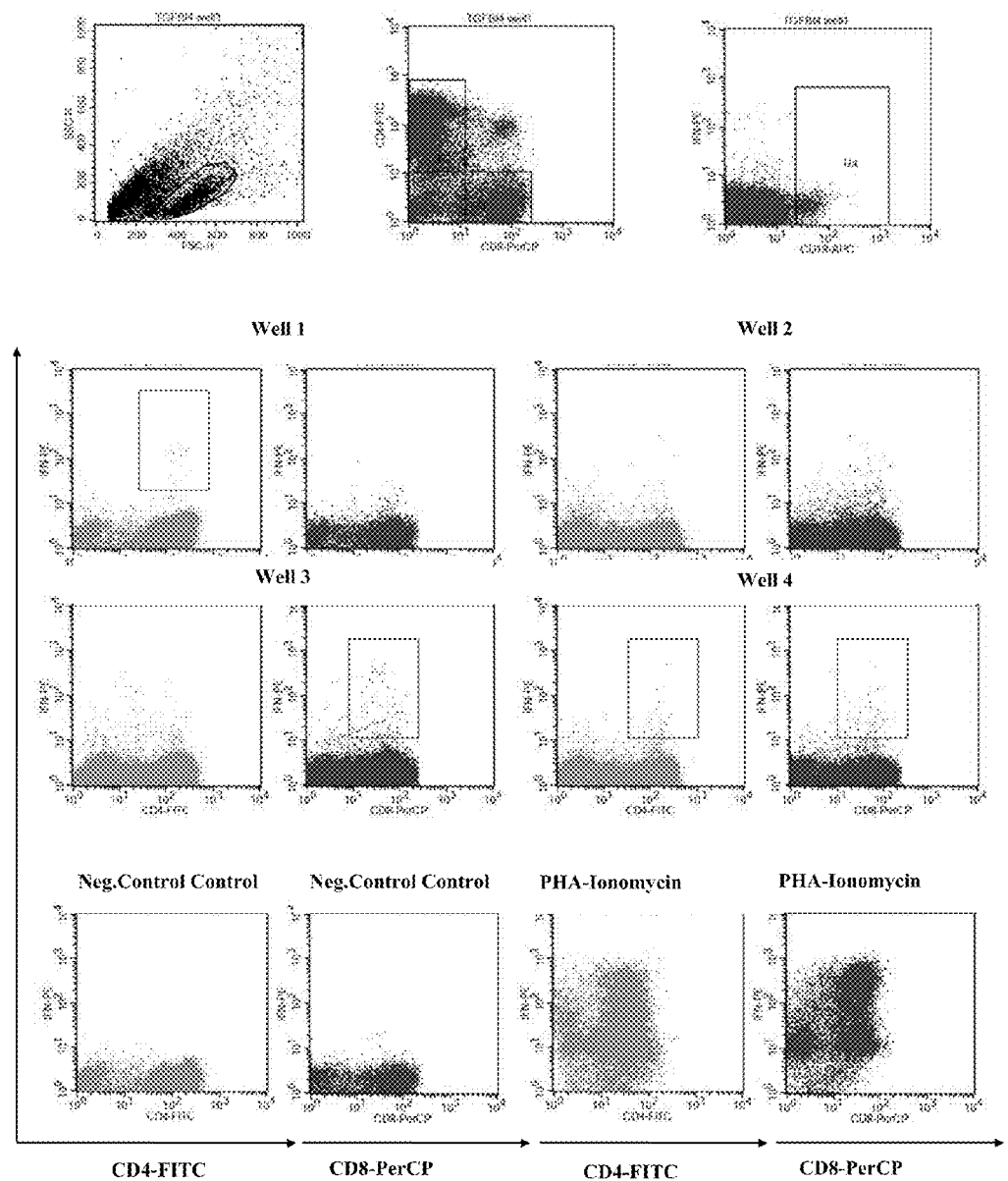
FIG. 3: In vitro immunogenicity of TGFBI-004 as detected by ICS after five stimulation cycles. Cells were primed with TGFBI-004-loaded autologous DCs and restimulated repeatedly with autologous PBMCs plus TGFBI-004. For the readout cells were incubated with relevant TGFBI-004 (Well 1, 2, 3 and 4) and irrelevant (Neg. Control) peptide, respectively. Additionally to the intracellular IFNγ staining, cells were also stained with CD4-FITC and CD8-PerCP antibodies. The analysis was performed on a four-color FACSCalibur cytometer (BD Biosciences, Germany).

It was possible to prime CD4+ T cell lines specifically reacting to the peptide of interest (FIG. 2 and FIG. 3). T-cell responses could be detected via ELISPOT in 2 out of 4 T-cell lines, whereas in 3 out of 4 T-cell lines TGFBI-004 specific IFN$\gamma$ producing CD4+ and/or CD8+ cells were shown via ICS.

Thus, TGFBI-004 was able to elicit CD4+ and CD8+ T cell responses in one donor tested with the above described experimental system. According to this promising result, it is likely that this peptide is immunogenic and has the capacity to induce T-cell responses.

Example 5

Functional Validation Exemplified by NOX-001 and TGFBI-001

Immunogenicity of peptides included in IMA910-A vaccine was demonstrated in vitro by using Immatics' TUMAP validation platform. The induction of specific T cells is an indication for the ability of peptides to successfully activate the immune system. Since efficient anti-tumor immune response is only possible when activated T cells are of high avidity and functional, we further investigated the TUMAPs to prime high avidity, functional T lymphocytes by their ability to produce IFNγ or to kill tumor cell lines. Two peptides, NOX-001 and TGFBI-001, were chosen for deeper validation due to their capacity to induce high avidity CTLs in vitro. We were able to prove that high avidity precursor T cells exist against both peptides in humans and that functional CD8+ T cell lines could be generated by NOX-001.

Principle of Test

To get additional insight on the immunogenicity of IMA910-A peptides and the properties of specific T cells, two peptides, NOX-001 and TGFBI-001, were selected for further evaluation. The experiments performed for this purpose were conducted at Immatics (cell sorting was performed at the University of Tübingen, lab of Dr. Bühring).

Dependent on their ability to be activated by high- or low-density antigen, T cell lines can be divided into high- or low-avidity. As it has been shown before (Walter, S, et al., 2003, J. Immunol., 171, 4974-4978), human high-avidity CTLs can be raised successfully by using less peptide for activation compared to low-avidity CD8+ T cells. It has also been demonstrated that cells expanded this way are more efficient in recognizing antigen-expressing tumor cell lines, hereby constituting a possible major tool in the development of therapy staratgies.

To be able to determine the ability of peptides to generate high-avidity CTL lines, isolated human CD8+ cells were primed and expanded by repeated in vitro stimulations with beads coated with low-density pMHC (peptide-MHC-complex) and anti-CD28 antibody in the presence of IL-12 and IL-2. After three stimulations, a fraction of in vitro primed T cells were pMHC-tetramer stained and detected by cytometric analysis. Tetramer-positive cells of each donor were pooled afterwards according to the antigen specificity, stained with pMHC-tetramer and human anti-CD8-FITC antibody and finally subjected to FACS sorting on a FACS Aria. Sorted cells were cultured and expanded in the presence of irradiated feeder cells, cytokines and mitogen. As a read-out for the generation of primed high avidity antigen specific cells, pMHC-tetramer staining was performed. To determine their functionality, IFNγ production was assayed by ELISPOT and killing of tumor cell lines was examined using a cytotoxicity assay based on live/dead staining after restimulation of the cells with the corresponding peptide and tumor cell lines.

Generation of Specific CD8+ T-cell Lines

In vitro stimulations using artificial antigen presenting cells (aAPC) loaded with peptide-MHC complex (pMHC) and anti-CD28 antibody were conducted as detailed above. The only difference to the method described there was the fact that stimulations were performed with beads loaded with 2 ng relevant plus 200 ng irrelevant library (PMHC)MHC (low density beads) instead of 200 ng relevant MHC (high density beads). Thus, predominantly high avidity T cells were generated for deeper validation of peptides. After three stimulations, a fraction of in vitro primed T cells was pMHC-tetramer stained and detected by cytometric analysis. Immunogenicity for a given antigen was detected if at least one evaluable in vitro stimulated well of one healthy donor was found to contain a specific CD8+ T-cell line after in vitro stimulation (i.e. this well contained at least 1% of specific tetramer+ among CD8+ T-cells and the percentage of specific tetramer+ cells was at least 10× the median of the negative control stimulations). Tetramer-positive cells of each donor were pooled afterwards according to the antigen specificity, stained with the corresponding pMHC-tetramer and human anti-CD8-FITC antibody clone SKI and finally subjected to FACS sorting on a FACSAria (BD Biosciences, Germany). Sorted cells were cultured in T cell medium (RPMI-Glutamax supplemented with 10% heat inactivated human AB serum, 100 U/ml penicillin, 100 µg/ml streptomycin, 1 mM sodium pyruvate and 20 µg/ml Gentamycin) in the presence of 5×10⁵ cells/ml irradiated fresh allogeneic PBMCs, 5×10⁴ cells/ml irradiated LG2-EBV cells, 150 U/ml IL-2 (Chiron, Munich, Germany) and 0.5 µg/ml PHA-L (Roche Diagnostics, Mannheim, Germany). Expansion of these cells occurred in T cell medium containing 150 U/ml IL-2. As a read-out for the generation of primed high avidity antigen specific cells, pMHC-tetramer staining was performed as above and analyzed on a four-color FACSCalibur (BD Biosciences, Germany).

Functionality Tests

To determine their functionality, IFNγ production was assessed by ELISPOT (IFNγ ELISPOT Set, BD, Germany) after restimulation of the cells with the corresponding peptide. Additionally, cell-mediated cytotoxicity of specific CTLs was investigated by killing of tumor cell lines using the LIVE/DEAD cell-mediated cytotoxicity Kit (L7010, Invitrogen, Germany). Both assays were performed according to manufacturer's instructions, except noted otherwise.

Results

Both peptides, NOX-001 and TGFBI-001, were immunogenic in vitro as shown by successful priming with low pMHC density aAPCs. For NOX-001 as well as for TGFBI-001 specific T-cell lines could be established by FACS, thus demonstrating that high-avidity CD8+ T cell precursors exist in healthy donors.

Figure 4:
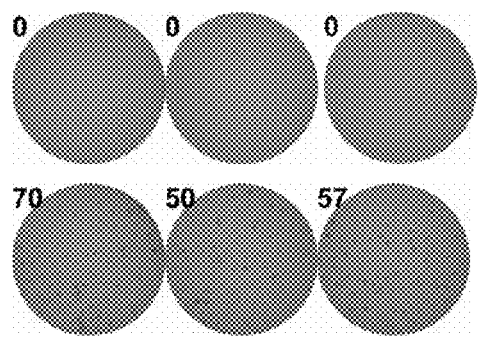
FIG. 4: ELISPOT analysis of IFNγ production by T-cell lines upon in vitro restimulation with the NOX-001 peptide. A. T-Cell line 7+ from donor HBC-154 (sorted CD8+ NOX-001 tetramer+); B. T-Cell line 7—from donor HBC-154 (sorted CD8+ NOX-001 tetramer−). Sorted CD8+ NOX-001 tetramer+ (A.) and CD8+ NOX-001 tetramer− (B.) cells were analyzed by IFNγ ELISPOT after restimulation with irrelevant (MLA-001) (upper wells) and relevant (NOX-001) (lower wells) peptide (10 µg/ml). Numbers indicate the count of positive spots.
Figure 4:
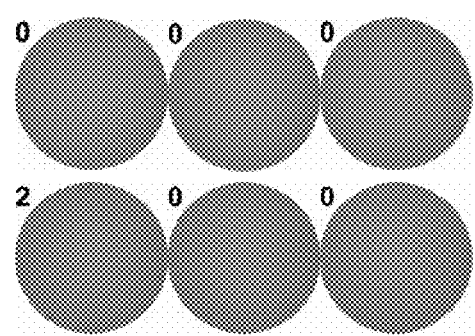

Additionally, for NOX-001, one T-cell line could be established that also proved to be functional by ELISPOT since it was specifically expressing IFNγ after restimulation with this peptide (FIG. 4).

Example 6

Synthesis of a Vaccine Comprising Some of the Peptides of the Present Invention

Synthesis and Structure

Peptides were synthesized by standard and well-established solid phase synthesis using Fmoc chemistry. After purification by preparative HPLC, ion-exchange procedure was performed to incorporate physiological compatible counter ions (acetate or chloride). Finally, white to off white solids were obtained after lyophilization. All TUMAPs are administered as acetate salts except IMA-CCN-001 which is supplied as chloride salt for technical reasons during the manufacturing procedure.

Importantly, identity and purity of the peptides can be determined easily and with high accuracy using mass spectrometry, amino acid analysis and analytical HPLC. According to analytical results, all peptides used for IMA910 vaccine show the correct structure with purities≧95%.

TABLE 6

Physico-chemical characteristics of peptides in vaccine IMA910

| No. | Peptide ID | Peptide length (no of amino acids) | Salt form | Physical form | Hygroscopicity |
|---|---|---|---|---|---|
| 1 | IMA-C20-001 | 9 | Acetate | White | Stored as |
| 2 | IMA-CCN-001 | 9 | Chloride | to off- | freeze |

TABLE 6-continued

Physico-chemical characteristics of peptides in vaccine IMA910

| No. | Peptide ID | Peptide length (no of amino acids) | Salt form | Physical form | Hygroscopicity |
|---|---|---|---|---|---|
| 3 | IMA-CEA-004 | 9 | Acetate | white powder | dried powder. Lyophilized peptides generally have hygroscopic properties. |
| 4 | IMA-CEA-006 | 16 | Acetate | | |
| 5 | IMA-HBV-001 | 10 | Acetate | | |
| 6 | IMA-MET-001 | 9 | Acetate | | |
| 7 | IMA-MMP-001 | 16 | Acetate | | |
| 8 | IMA-MUC-001 | 9 | Acetate | | |
| 9 | IMA-NOX-001 | 9 | Acetate | | |
| 10 | IMA-ODC-001 | 9 | Acetate | | |
| 11 | IMA-PCN-001 | 10 | Acetate | | |
| 12 | IMA-TGFBI-001 | 10 | Acetate | | |
| 13 | IMA-TGFBI-004 | 15 | Acetate | | |
| 14 | IMA-TOP-001 | 10 | Acetate | | |

Particle size distribution and particle shape measurement of the particles obtained after reconstitution have been performed by capturing direct images of each individual particle in the range of 0.25 to 100 µm followed by image analysis. As a result the majority (>95%) of the particles have been found in the range of 0.25 to 2.7 µm. So far, no major differences in size and shape distribution could be observed within 1, 2 or 3 hours after reconstitution.

Furthermore, analytical HPLC was performed for a closer characterization of the obtained suspension. It could be demonstrated that the particles consist mainly of two peptides (IMA-TGFBI-001 and IMA-NOX-001) which are almost insoluble in the solution used for reconstitution of IMA910. Additionally, low amounts of 4 other peptides (IMA-CEA-006, IMA-TOP-001, IMA-CCN-001 and IMA-HBV-001) were also found in the particles. The composition of the particles (qualitatively and quantitatively) was found to be very similar in two independently manufactured batches.

Mannitol and Polysorbate 80 (Tween 80) have been used as excipients and non-active ingredients to improve solubility characteristics of the peptide lyophilisate.

IMA910 is dissolved in 700 µL sodium hydrogen carbonate (4.2%).

To reconstitute IMA910, 700 µL of the diluent is injected through the stopper into the vial by a 1 mL syringe equipped with a needle. To dissolve IMA910, the vial and the diluent shall be shaken gently for about 2 minutes. Shaking should be performed carefully to avoid strong foaming. By this procedure a white to off-white homogeneous suspension will be obtained. To avoid any sedimentation the vial content shall be gently shaken before transferring 500 µL of this suspension into a new syringe equipped with a needle (size: G20). 10 to 30 minutes after GM-CSF injection administer 500 µL reconstituted IMA910 i.d. at the same injection site. Administration has to occur within 1 h after reconstitution. Dissolved lyophilisate may be stored aseptically at room temperature for up to 1 hour following reconstitution.

IMA910 is composed of a cocktail of 13 synthetic tumor-associated peptides (TUMAPs) of which the majority has been identified on primary colorectal carcinoma (CRC) cells. The TUMAPs include 10 HLA class I-binding peptides with the capacity to activate cytotoxic T cells (CD8+ T cells) and 3 HLA class II-binding peptides with the capacity to activate T helper cells (CD4+ T cells). In addition to these 13 TUMAPs IMA910 contains one control peptide of viral origin.

Example 7

Binding of HLA Class I-restricted Peptides of the Invention to HLA-A*0201

The objective of this analysis was to evaluate the affinity of the HLA class I peptides to the MHC molecule coded by the HLA-A*0201 allele as this is an important parameter for the mode of action of IMA910. Affinities to HLA-A*0201 were high for 9 of 10 HLA class I-restricted peptides in IMA910, dissociations constants (KD) being in the range from 0.001 to 0.2 nM. Also the viral marker peptide IMA-HBV-00 1 showed strong binding. Affinity for IMA-MUC-001 was about two decades weaker. These results confirmed the strong binding affinity of 9 out of 10 HLA class I peptides of the IMA910 vaccine candidate to MHC molecules. See FIG. 7.

Principle of Test

Stable HLA/peptide complexes consist of three molecules: HLA heavy chain, beta-2 microglobulin (b2m) and the peptidic ligand. The activity of denatured recombinant HLA-A*0201 heavy chain molecules alone can be preserved making them functional equivalents of "empty HLA-A*0201 molecules." When diluted into aqueous buffer containing b2m and an appropriate peptide, these molecules fold rapidly and efficiently in an entirely peptide-dependent manner. The availability of these molecules is used in an ELISA-based assay to measure the affinity of interaction between peptide and HLA class I molecule (Sylvester-Hvid et al., 2002). Purified recombinant HLA-A*0201 molecules were incubated together with b2m and graded doses of the peptide of interest. The amount of de novo-folded HLA/peptide complexes was determined by a quantitative ELISA. Dissociation constants (KD values) were calculated using a standard curve recorded from dilutions of a calibrant HLA/peptide complex.

Results

Figure 7:
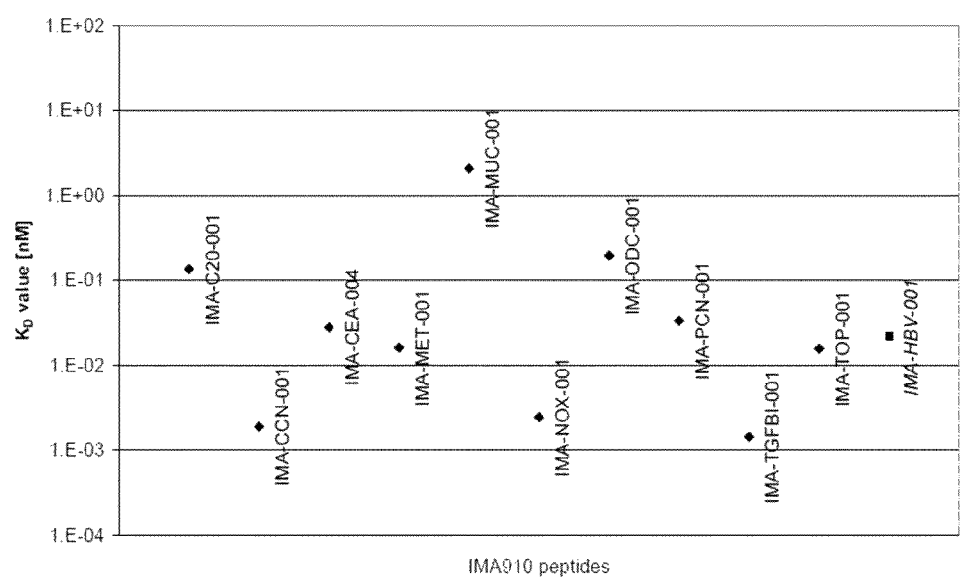
FIG. 7: shows the results of affinity testing to HLA-A*0201 for peptides of the present invention.

Results are shown in FIG. 7. A lower KD value reflects higher affinity to HLA-A*0201. Most of the IMA910 peptides and the viral control peptide IMA-HBV-001 had similar and strong affinities to HLA-A*0201 within the range from 0.001 (IMA-TGFBI-001) to 0.2 nM (IMA-ODC-001). Affinity of IMA-MUC-001 was about two to three decades lower as compared to the majority of the included ligands. However, vaccination with IMA-MUC-001 led to immune responses in renal cell carcinoma patients in an earlier clinical trial conducted by immatics, thus the lower binding affinity of IMA-MUC-001 gives no cause for concern.

The invention claimed is:

1. A pharmaceutical composition comprising at least two peptides and a pharmaceutically acceptable carrier, wherein each of the at least two peptides has an overall length of not more than 100 amino acids and each of the at least two peptides comprises an amino acid sequence selected from the group consisting of SEQ ID NO: 1 to SEQ ID NO: 7.

2. The pharmaceutical composition according to claim 1, further comprising at least one additional peptide having an overall length of not more than 100 amino acids comprising an amino acid sequence selected from the group consisting of SEQ ID NO: 8 to SEQ ID NO: 15.

3. The pharmaceutical composition according to claim 1, wherein at least one of the at least two peptides includes a non-peptide bond.

4. The pharmaceutical composition according to claim 2, wherein at least one of the said at least two peptides consists of an amino acid sequence selected from the group consisting of SEQ ID NO: 1 to SEQ ID 7 and said at least one further peptide consists of an amino acid sequence selected from the group consisting of SEQ ID NO 8 to SEQ ID NO: 15.

5. The pharmaceutical composition according claim 1, comprising 13 peptides according to SEQ ID NO: 1 to SEQ ID NO: 11, SEQ ID NO: 13 and SEQ ID 15, and a viral marker.

6. The pharmaceutical composition according to claim 5, wherein the viral marker is HVB001 according to SEQ ID NO:14.

7. The pharmaceutical composition according to claim 1, wherein the peptides of the composition are cancer specific.

8. The pharmaceutical composition according to claim 1, wherein each of the peptides is present in an amount from about 1500 μg to about 75 μg.

9. The pharmaceutical composition according to claim 1, further comprising at least one suitable adjuvant.

10. The pharmaceutical composition according to claim 9, wherein the adjuvant is Granulocyte Macrophage Colony Stimulating Factor (GM-CSF).

11. The pharmaceutical composition according to claim 1, additionally comprising at least one antigen presenting cell.

12. The pharmaceutical composition according to claim 11, wherein the antigen presenting cell is a dendritic cell.

13. The pharmaceutical composition according to claim 11, wherein the at least one antigen presenting cell is
   a. pulsed or loaded with the peptide or
   b. comprises an expression construct encoding the peptide.

14. The pharmaceutical composition according to claim 1, wherein the composition is capable of being administered intravenously, intra-arterially, intra-peritoneally, intramuscularly, intradermally, intratumorally, orally, dermally, nasally, buccally, rectally, vaginally, by inhalation, or by topical administration.

15. A method for inducing an immune response in a patient comprising administering to the patient a therapeutically effective amount of the pharmaceutical composition of claim 1.

16. The method according to claim 15, wherein the pharmaceutical composition is a vaccine.

17. The method of claim 16, wherein the patient is experiencing at least one disease selected from the group consisting of: cancer of the buccal cavity or pharynx; cancer of the digestive tract; cancer of the colon, rectum, or anus; cancer of the respiratory tract; breast cancer; cancer of the cervix uteri, vagina, or vulva; cancer of the uterine corpus or ovary; cancer of the male genital tract; cancer of the urinary tract; cancer of the bone or soft tissue; Kaposi sarcoma; melanoma of the skin, eye melanoma, or non-melanoma eye cancer; cancer of the brain and central nervous system; cancer of the thyroid or other endocrine glands, Hodgkin Lymphoma, Non-Hodgkin Lymphoma, or myeloma; renal cancer; colorectal cancer; lung cancer; pancreatic cancer; prostate cancer; gastric cancer; GIST; and glioblastoma.

18. The method according to claim 17, wherein the disease is colorectal cancer.

19. The method of claim 15 wherein said pharmaceutical composition is administered directly to the patient.

20. The method of claim 15 wherein said pharmaceutical composition is administered by a method comprising:
   a. administering said pharmaceutical composition ex vivo to immune cells derived from the patient; and
   b. transplanting said immune cells into the patient.

21. The method of claim 15 wherein said pharmaceutical composition is administered by a method comprising:
   a. administering said pharmaceutical composition in vitro to a human cell line; and
   b. transplanting said cell line into the patient.

22. A method for activating a subpopulation of cytotoxic T-lymphocytes in a patient comprising administering to the patient a therapeutically effective amount of the pharmaceutical composition of claim 1.

* * * * *

SEQUENCE LISTING

<160> NUMBER OF SEQ ID NOS: 15

<210> SEQ ID NO 1
<211> LENGTH: 9
<212> TYPE: PRT
<213> ORGANISM: homo sapiens

```
<400> SEQUENCE: 1

Ala Leu Ser Asn Leu Glu Val Thr Leu
1               5

<210> SEQ ID NO 2
<211> LENGTH: 9
<212> TYPE: PRT
<213> ORGANISM: homo sapiens

<400> SEQUENCE: 2

Ile Leu Ala Pro Val Ile Leu Tyr Ile
1               5

<210> SEQ ID NO 3
<211> LENGTH: 9
<212> TYPE: PRT
<213> ORGANISM: homo sapiens

<400> SEQUENCE: 3

Ile Leu Asp Gln Lys Ile Asn Glu Val
1               5

<210> SEQ ID NO 4
<211> LENGTH: 10
<212> TYPE: PRT
<213> ORGANISM: homo sapiens

<400> SEQUENCE: 4

Lys Leu Met Asp Leu Asp Val Glu Gln Leu
1               5                   10

<210> SEQ ID NO 5
<211> LENGTH: 10
<212> TYPE: PRT
<213> ORGANISM: homo sapiens

<400> SEQUENCE: 5

Ala Leu Phe Val Arg Leu Leu Ala Leu Ala
1               5                   10

<210> SEQ ID NO 6
<211> LENGTH: 10
<212> TYPE: PRT
<213> ORGANISM: homo sapiens

<400> SEQUENCE: 6

Lys Ile Phe Asp Glu Ile Leu Val Asn Ala
1               5                   10

<210> SEQ ID NO 7
<211> LENGTH: 15
<212> TYPE: PRT
<213> ORGANISM: homo sapiens

<400> SEQUENCE: 7

Thr Pro Pro Ile Asp Ala His Thr Arg Asn Leu Leu Arg Asn His
1               5                   10                  15

<210> SEQ ID NO 8
<211> LENGTH: 16
<212> TYPE: PRT
<213> ORGANISM: homo sapiens

<400> SEQUENCE: 8
```

```
Ser Pro Gln Tyr Ser Trp Arg Ile Asn Gly Ile Pro Gln Gln His Thr
1               5                   10                  15

<210> SEQ ID NO 9
<211> LENGTH: 9
<212> TYPE: PRT
<213> ORGANISM: homo sapiens

<400> SEQUENCE: 9

Leu Leu Gly Ala Thr Cys Met Phe Val
1               5

<210> SEQ ID NO 10
<211> LENGTH: 9
<212> TYPE: PRT
<213> ORGANISM: homo sapiens

<400> SEQUENCE: 10

Ser Thr Ala Pro Pro Val His Asn Val
1               5

<210> SEQ ID NO 11
<211> LENGTH: 16
<212> TYPE: PRT
<213> ORGANISM: homo sapiens

<400> SEQUENCE: 11

Ser Gln Asp Asp Ile Lys Gly Ile Gln Lys Leu Tyr Gly Lys Arg Ser
1               5                   10                  15

<210> SEQ ID NO 12
<211> LENGTH: 9
<212> TYPE: PRT
<213> ORGANISM: homo sapiens

<400> SEQUENCE: 12

Tyr Leu Ser Gly Ala Asp Leu Asn Leu
1               5

<210> SEQ ID NO 13
<211> LENGTH: 9
<212> TYPE: PRT
<213> ORGANISM: homo sapiens

<400> SEQUENCE: 13

Tyr Val Asp Pro Val Ile Thr Ser Ile
1               5

<210> SEQ ID NO 14
<211> LENGTH: 10
<212> TYPE: PRT
<213> ORGANISM: homo sapiens

<400> SEQUENCE: 14

Phe Leu Pro Ser Asp Phe Phe Pro Ser Val
1               5                   10

<210> SEQ ID NO 15
<211> LENGTH: 9
<212> TYPE: PRT
<213> ORGANISM: homo sapiens

<400> SEQUENCE: 15

Tyr Leu Ser Gly Ala Asn Leu Asn Leu
1               5
```